(12) United States Patent
Lampe et al.

(10) Patent No.: US 8,117,854 B2
(45) Date of Patent: Feb. 21, 2012

(54) SYSTEM AND METHOD FOR PRODUCING AND DETERMINING COOLING CAPACITY OF TWO-PHASE COOLANTS

(75) Inventors: Joshua W. Lampe, Philadelphia, PA (US); Lance B. Becker, Philadelphia, PA (US); Diana Bull, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 12/738,417

(22) PCT Filed: Oct. 20, 2008

(86) PCT No.: PCT/US2008/080435
§ 371 (c)(1),
(2), (4) Date: Jul. 15, 2010

(87) PCT Pub. No.: WO2009/052470
PCT Pub. Date: Apr. 23, 2009

(65) Prior Publication Data
US 2010/0308257 A1    Dec. 9, 2010

Related U.S. Application Data

(60) Provisional application No. 60/981,357, filed on Oct. 19, 2007, provisional application No. 61/037,949, filed on Mar. 19, 2008.

(51) Int. Cl.
*F25C 1/00* (2006.01)
(52) U.S. Cl. ............................................. 62/74; 62/340
(58) Field of Classification Search ................ 62/74, 68, 62/123, 340, 434, 532; 165/104.31, 299; 252/71; 422/307
See application file for complete search history.

(56) References Cited

U.S. PATENT DOCUMENTS

| | | | | |
|---|---|---|---|---|
| 3,675,436 A | * | 7/1972 | Ganiaris | 62/535 |
| 3,712,075 A | * | 1/1973 | Smith et al. | 62/123 |
| 3,835,658 A | * | 9/1974 | Wilson | 62/535 |
| 4,043,501 A | * | 8/1977 | Larrabee et al. | 229/117.27 |
| 4,049,192 A | * | 9/1977 | Krebs et al. | 494/37 |
| 4,754,610 A | | 7/1988 | Knodel et al. | |
| 5,435,155 A | | 7/1995 | Paradis | |
| 6,218,100 B1 | * | 4/2001 | Wollowitz et al. | 435/2 |
| 6,244,052 B1 | | 6/2001 | Kasza | |
| 6,305,178 B1 | * | 10/2001 | Shi et al. | 62/123 |
| 6,367,268 B1 | * | 4/2002 | Paul | 62/59 |
| 6,413,444 B1 | | 7/2002 | Kasza | |
| 6,547,811 B1 | | 4/2003 | Becker et al. | |
| 7,118,591 B2 | * | 10/2006 | Frank et al. | 607/105 |
| 2003/0066304 A1 | | 4/2003 | Becker et al. | |
| 2005/0082047 A1 | | 4/2005 | Kaellis | |
| 2005/0090881 A1 | * | 4/2005 | Frank et al. | 607/105 |
| 2005/0203598 A1 | | 9/2005 | Becker et al. | |
| 2006/0036302 A1 | | 2/2006 | Kasza et al. | |
| 2006/0062273 A1 | | 3/2006 | Egolf et al. | |
| 2006/0136023 A1 | | 6/2006 | Dobak, III | |
| 2006/0153921 A1 | | 7/2006 | Chattopadhyay et al. | |
| 2006/0161232 A1 | | 7/2006 | Kasza et al. | |
| 2006/0253095 A1 | * | 11/2006 | Stull | 604/500 |

OTHER PUBLICATIONS

International Search Report for International Appl. No. PCT/US2008/080435; dated Apr. 21, 2009.

(Continued)

*Primary Examiner* — Mohammad Ali
(74) *Attorney, Agent, or Firm* — RatnerPrestia

(57) ABSTRACT

The invention provides systems and devices for producing two-phase coolants such as an ice slurry. Also provided are methods for producing two-phase coolants, and methods for using the two-phase coolants to lower the temperature or maintain a low temperature in any subject, system, object, device, or application where particular low temperatures are desired. Also provided are systems for determining the cooling capacity of two-phase coolants.

13 Claims, 10 Drawing Sheets

OTHER PUBLICATIONS

International Search Report for International Appl. No. PCT/US2009/037679; dated May 5, 2009.

Peter W. Egolf, et al.; Thermodynamics and heat transfer of ice slurries; International Journal of Refrigeration 28; pp. 51-59; vol. 28 (2005); Elsevier Ltd. And IIR.

Joshua W. Lampe et al.; Rapid cooling for saving lives: a bioengineering opportunity; Expert Rev. Med Devices 4(4); 2007; pp. 441-446; Future Drugs Ltd.

Brett A. Laven et al.; A pilot study of ice-slurry application for inducing laparoscopic renal hypothermia; Journal Compilation 2006; pp. 166-170; vol. 99; BJU International.

Marcelo A. Orvieto et al.; Laparoscopic Ice Slurry Coolant for Renal Hypothermia; The Journal of Urology; vol. 177; Jan. 2007; pp. 382-385; American Urological Association.

Terry L. Vanden Hoeck, MD et al.; Induced hypothermia by central venous infusion: Saline ice slurry versus chilled saline; Critical Care Medicine 2004; vol. 32, No. 9 (Suppl.); pp. S425-S431; Lippencott Williams & Wilkins.

* cited by examiner

PRESSURE FEED FOR LIQUID PUMPING

SYSTEM AND METHOD FOR PRODUCING AND DETERMINING COOLING CAPACITY OF TWO-PHASE COOLANTS

CROSS REFERENCE TO RELATED APPLICATIONS

This application is a U.S. National Phase Application of PCT International Application PCT/US2008/080435, filed Oct. 20, 2008, which claims priority to U.S. Provisional Application No. 60/981,357, filed Oct. 19, 2007, and U.S. Provisional Application No. 61/037,949, filed Mar. 19, 2008. The disclosure of each application is incorporated by reference herein, in its entirety and for all purposes.

FIELD

The invention relates generally to the field of refrigeration and cooling. More specifically, the invention relates to systems for producing a coolant such as a two-phase coolant and to systems for measuring the cooling capacity of coolants such as two-phase, liquid-solid coolants.

BACKGROUND

Numerous industries require cooling systems for a large variety of applications. In many cases, refrigerant chemicals or machines are used to generate cold air or ice for a desired application. Although various cooling systems have been proposed, there remains a need in the art for improved cooling systems.

SUMMARY

In one aspect, the invention provides systems for producing a two-phase coolant. The system comprises a first container, a homogenizer coupled to receive a first fluid from the first container, a valve positioned to control flow of the first fluid from the first container to the homogenizer and, a second container coupled to deliver a second fluid to the homogenizer. The first container can be configured to maintain the first fluid at a temperature below the atmospheric freezing point of the first fluid and can be pressurized at a level sufficiently high to cause substantially instantaneous freezing of the first fluid upon its release from the first container. The second container can be configured to maintain the second fluid at a temperature below the atmospheric freezing point of the first fluid. The homogenizer can comprise an aperture for efflux of the produced coolant.

In an additional aspect, the invention provides methods for producing a coolant such as a two-phase coolant. The methods comprise admixing a microparticalized solid produced by releasing from a pressurized container a first fluid cooled to a temperature below its atmospheric freezing point with a carrier fluid cooled to a temperature below the atmospheric freezing point of the first fluid. It is preferred that the pressure in the container is sufficiently high to cause substantially instantaneous freezing of the first fluid upon release from the container. In some aspects, the microparticalized solid is ice. The first fluid or carrier fluid can be aqueous or nonpolar. Aqueous fluids can be a physiologically compatible buffer, or can comprise one or more salts, sugars, biomolecules, surfactants, or emulsifiers.

The invention also provides methods for inducing hypothermia in a subject. The methods can comprise administering to the subject a pharmaceutically acceptable microparticulate two-phase coolant in an amount effective to induce hypothermia in the subject. The subject can be any animal, and is preferably a human being. The hypothermia can be systemic or can be localized to one or more particular organs, tissues, locations, cavities, spaces, or regions in the body.

The invention further provides methods for cooling perishable goods. The methods can comprise producing a microparticulate two-phase coolant and exposing perishable goods to the coolant. Perishable goods can be a food or beverage product, chemical, drug, or pharmaceutical compound or composition, cells, tissues, biological fluids, organs, and the like.

The invention further provides methods for cooling devices. In some preferred aspects, the devices are weapons. The methods can comprise producing a microparticulate two-phase coolant and exposing the device to the coolant. Exemplary weapons include guns, cannons, and weaponized lasers.

Also provided are methods for cooling rooms. Such methods can comprise producing a microparticulate two-phase coolant, exposing air to the coolant, and circulating the cooled air throughout at least one room.

In another aspect, the invention provides a system for determining the cooling capacity of a two-phase, solid-liquid coolant. A length of conduit with known heat transfer characteristics receives a flow of two-phase, solid-liquid coolant at a prescribed volumetric flow rate. A heat source is positioned to transfer heat to the coolant flowing through the interior of the conduit. At least one heat flux sensor and at least one temperature sensor are positioned on the conduit to measure heat transfer to the coolant and coolant temperature as functions of the distance traveled by the coolant through the conduit interior. Electronics coupled to the temperature and heat flux sensors compute the cooling capacity of the coolant using the heat transfer to the coolant and coolant temperature change measured in the conduit.

In an additional aspect, the invention provides a system to detect solid void fraction and solid particle size in a two-phase, solid-liquid coolant. A conduit of a predetermined length with known heat transfer characteristics having an interior and an exterior and an inlet and an outlet receives a flow of a two-phase, solid-liquid coolant at a prescribed volumetric flow rate. A heat source is positioned to transfer heat to the coolant flowing through the interior of the conduit. The conduit has at least one heat flux sensor positioned to measure heat transfer to the coolant as a function of distance traveled by the coolant through the conduit. The conduit further has at least one temperature sensor positioned to measure coolant temperature in the conduit interior as a function of distance traveled by the coolant through the conduit. Electronics coupled to the temperature and heat flux sensors determine the solid void fraction and solid particle size of the coolant using the measured heat transfer and temperature.

In an additional aspect, the invention provides a method of determining the cooling capacity of a two-phase, solid-liquid coolant. Heat is transferred to a prescribed volumetric flow of a two-phase, solid-liquid coolant flowing through a conduit of a predetermined length having an interior and an exterior and known heat transfer characteristics. The heat transfer to the flow of coolant in the conduit and the coolant to temperature are measured as a function of distance traveled by the coolant through the conduit. The cooling capacity of the coolant is calculated using the measured heat transfer and coolant temperature.

In an additional aspect, a method of detecting solid void fraction and solid particle size in a two-phase, solid-liquid coolant is provided. Heat is transferred to a prescribed volumetric flow of a two-phase, solid-liquid coolant flowing through a conduit of a predetermined length having an interior and an exterior and known heat transfer characteristics. The heat transfer to the flow of coolant in the conduit and the temperature of the coolant in the conduit are measured as a function of distance traveled by the coolant through the conduit. The measured heat transfer and coolant temperature are correlated with the coolant solid void fraction and solid particle size, and the coolant solid void fraction and solid particle size are calculated.

The invention also features systems and devices for producing a two phase coolant such as an ice slurry. In one aspect, a system for producing an ice slurry is provided, which comprises a low concentration saline, such as a commercially available, 0.45%, 0.9% or 3.0% physiological saline solution, a coolant such as dry ice or a compressed gas, a heat exchanger configured to control the freezing temperature of the low concentration saline, and a heat source positioned to heat the ice slurry that forms as the saline freezes. The heat exchanger can comprise two concentric tubes, with the inner tube configured for ice slurry formation and flow, and the outer tube configured to comprise the coolant for cooling the inner tube to allow a portion of the low concentration saline to freeze, resulting in an ice slurry comprising liquid phase and solid phase (frozen) low concentration saline solution. The ice slurry can comprise about 0.001%, 5%, 10%, 15%, 20%, 25%, 30%, 35%, 40%, 45%, 50%, 55%, 60%, 65%, 70%, 75%, 80%, 85%, 90%, 95%, or more solid phase ice. The heat exchanger can alternatively comprise a heat pipe such as an annular heat pipe.

In some aspects, devices for producing an ice slurry can comprise a housing comprising a heat exchanger comprising at least one coolant and configured to control the freezing temperature of a fluid such as a low concentration saline, a driveshaft which can be configured to rotate, at least one scraper blade coupled to the driveshaft and configured to scrape ice from the side walls of the heat exchanger, an internal disk coupled to the heat exchanger and configured to hold the bearing at an end of the driveshaft, a mixing vessel housing coupled to the housing comprising the heat exchanger and comprising a mixing vessel, and a mixing vessel configured to receive ice slurry from the heat exchanger and to receive a high concentration saline solution, and comprising a mixing blade.

The heat exchanger can comprise two concentric tubes, with the inner tube configured for ice slurry formation and flow, and the outer tube configured to comprise the coolant for cooling the inner tube to allow a portion of the low concentration saline to freeze, resulting in a low concentration saline-ice slurry comprising liquid phase saline and solid phase ice. The heat exchanger can alternatively comprise a heat pipe such as an annular heat pipe. The low concentration saline can be a commercially available, medical grade saline solution such as a 0.45%, 0.9%, or 3.0% physiological saline solution. The high concentration saline can be a commercially available, medical grade saline solution such as 3.0%, 5.0%, or 7.5%% physiological saline solution.

The device can further comprise pumps. For example, the device can comprise a first pump configured to transport the ice slurry through one or more components of the device, and can comprise a second pump configured to pump coolant through the heat exchanger. Any suitable coolant can be used, such as dry ice, dry ice-alcohol slurry, a compressed gas, freezing point depressed water, ethylene glycol, or polyethylene glycol.

The invention also provides kits for producing an ice slurry, for example, by using the systems, devices, and methods described and exemplified herein. In some aspects, the kits comprise a low concentration saline solution, at least one coolant, a heat exchanger configured to control the freezing temperature of the saline, and a high concentration saline solution. The coolant can be any suitable coolant such as dry ice or a compressed gas. The low concentration saline can be a commercially available, medical grade saline solution such as a 0.45%, 0.9%, or 3.0% physiological saline solution. The high concentration saline can be a commercially available, medical grade/physiological saline solution.

The heat exchanger can comprise two concentric tubes, with the inner tube configured for ice slurry formation and flow, and the outer tube configured to comprise the coolant for cooling the inner tube to allow a portion of the low concentration saline to freeze, resulting in an ice slurry comprising liquid phase saline solution and a solid phase of ice. The heat exchanger can alternatively comprise a heat pipe such as an annular heat pipe.

The invention also provides methods for producing an ice slurry. Generally, the methods comprise contacting a low concentration saline solution with a heat exchanger comprising at least one coolant and configured to control the freezing temperature of the saline solution. Upon contact of the saline solution with the heat exchanger, a portion of the saline solution freezes within the heat exchanger, and the remainder of the saline solution remains in the liquid state to form an ice slurry. After formation of the ice slurry, the methods comprise the step of admixing a high concentration saline solution with the ice slurry.

The heat exchanger can comprise two concentric tubes, with the inner tube configured for ice slurry formation and flow, and the outer tube configured to comprise the coolant for cooling the inner tube to allow a portion of the low concentration saline to freeze, resulting in an ice slurry comprising liquid phase and frozen low concentration saline solution. The heat exchanger can alternatively comprise a heat pipe such as an annular heat pipe. The low concentration saline can be a commercially available, medical grade saline solution such as a 0.45%, 0.9%, or 3.0% physiological saline solution. The high concentration saline can be a commercially available, medical grade saline solution such as a 3.0%, 5.0%, or 7.5% physiological saline solution. The ice slurry can comprise about 0.001%, 5%, 10%, 15%, 20%, 25%, 30%, 35%, 40%, 45%, 50%, 55%, 60%, 65%, 70% or more solid phase saline.

The invention also provides methods for inducing hypothermia in a subject. The methods comprise administering to the subject an effective amount of a pharmaceutically acceptable ice slurry produced by contacting a low concentration saline solution with a heat exchanger comprising at least one coolant and configured to control the freezing temperature of the saline solution wherein a portion of the saline solution freezes within the heat exchanger, and the remainder of the saline solution remains in the liquid state to form an ice slurry, and admixing a high concentration saline solution with the ice slurry. The subject can be any animal and is preferably a human. The hypothermia can be systemic throughout the body of the subject, or can be localized to a particular organ, tissue, location, cavity, space or region in the body of the subject.

DETAILED DESCRIPTION

Figure 1:
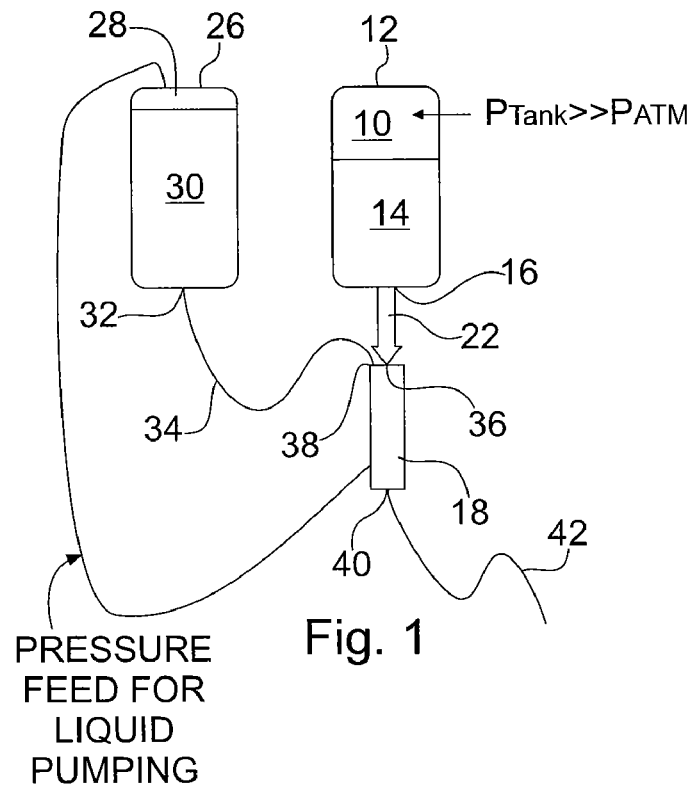
FIG. 1 shows a schematic view of an exemplary embodiment of a two-phase coolant production system.

Various terms relating to the systems, methods, and other aspects of the present invention are used throughout the specification and claims. Such terms are to be given their ordinary meaning in the art unless otherwise indicated.

Various publications, including patents, published applications, technical articles and scholarly articles are cited throughout the specification. Each of these cited publications is incorporated by reference herein, in its entirety and for all purposes.

It has been discovered in accordance with aspects of the present invention that freezing point depression can be harvested to spontaneously freeze a fluid, which can be microparticlized and mixed with a carrier fluid to form an ice slurry. It has further been discovered that the size of the microparticles can be controlled and fine-tuned to serve a particular application. In addition, it has been discovered that the resultant slurry can be maintained and transported in a controlled environment to prevent undesired melting of the frozen particles, to prevent clumping, and to prevent intermixing of the frozen fluid contents with the carrier fluid. It has also been discovered that the admixing of salt after the formation of ice crystals in commercially available ice slurry production devices will render the slurry more pumpable.

Accordingly, the invention provides cooling systems, including systems for producing a two-phase coolant. The figures illustrate exemplary embodiments of the inventive systems. In one exemplary aspect shown in FIG. 1, the system comprises a first container 10. The first container comprises at least one aperture 12 for introducing first fluid 14 into the container. First fluid 14 is releasably retained within the container 10. First container 10 also comprises at least one additional aperture 16 for releasing first fluid 14 from the container. First container 10 is coupled to homogenizer 18 such that first fluid 14 is received by the homogenizer. Optionally, first container 10 is coupled to homogenizer 18 by a first tube 20.

In some aspects, the system comprises valve 22 positioned to control flow of the first fluid 14 from the first container 10 to the homogenizer 18. The valve can optionally be coupled to container 10, first tube 20, or homogenizer 18. A gasket 24, which is optional, can be attached to the first container 10 at second aperture 16, to first tube 20, to valve 22, or to homogenizer 18. Since the couplings of the constituents of the system may not completely form a fluid or airtight seal, gasket 24 is utilized to form a seal between the coupled constituents.

The valve 22 can be a nozzle. An atomizer or nozzle can be used to create micron-sized droplets of the fluid of interest. The fluid is expected to undergo phase transition from liquid to solid when released from the nozzle once droplet pressure returns to atmospheric.

Figure 4A:
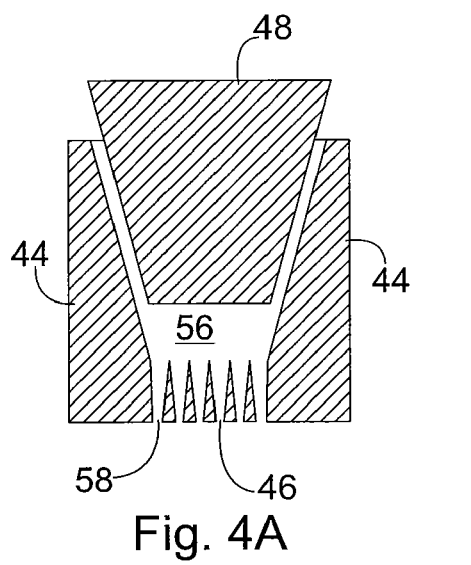
FIG. 4A-C shows a schematic diagram of two nozzle embodiments adapted for the generation of ice from a pressurized liquid. The shaded areas are surfaces that may be heated or coated with non-stick substances to impede internal ice formation and blockage of the nozzle outlets.
Figure 4B:
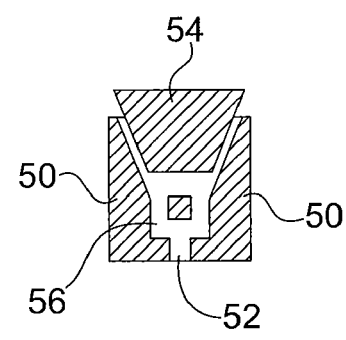
Figure 4C:
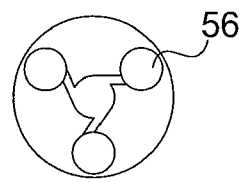

FIG. 4 shows a schematic diagram of exemplary nozzle structures that may be used in the present invention to facilitate particlized ice production. FIG. 4A shows a cross section of a nozzle with multiple apertures. FIG. 4B shows a cross section of a nozzle with a single aperture. FIG. 4C shows a top view of the single aperture nozzle. The nozzle 44, for example, can have a plurality of small apertures 46 present to form a fine mist from the exiting fluid. A needle valve 48 can be used to restrict flow of fluid through the nozzle to control flow rate. In another example, the nozzle 50 has only a single aperture 52, but has internal geometry such that the liquid exiting the hole will have substantial rotational velocity, dramatically increasing the kinetic energy present in the flow, thereby resulting in the formation of a fine mist. Nozzle 50 can also comprise a needle valve 54 to control fluid flow through the nozzle.

It is preferred that the nozzle maintains high enough pressure through the fluid's exit such that the fluid will not begin to change phase, e.g., freeze, inside of the nozzle. Solidification of the fluid inside the nozzle can potentially cause clogging of the fluid flow space 56 of the nozzle or clogging of the apertures. To reduce the possibility of phase change occurring before the fluid exits the nozzle, the apertures 46 can be cone-shape, with the outlet 58 being the narrowest diameter.

In the event that a cone-shape is insufficient to keep the fluid from freezing in the nozzle, at least two non-limiting alternative strategies can be used to reduce or eliminate solidification and nozzle obstruction. The first is to use resistive heating elements (not shown) to create a small thermal boundary layer in the flow near the nozzle wall 56. This boundary layer will not freeze, and can keep the flow continuing smoothly through the exit. The second is to use a hydrophobic coating on the nozzle to reduce the adhesion energy between the exiting fluid and the nozzle wall. This hydrophobic coating can also attract other hydrophobic elements that may be present in the exiting liquid, which can further serve to reduce the adhesion energy between the exiting fluid and the nozzle wall.

As shown in FIG. 1, the system also comprises second container 26. Second container 26 can be separate from or concentric with or otherwise associated with first container 10. FIG. 1 shows the separate configuration of the two containers. The second container comprises at least one aperture 28 for introducing second fluid 30 into the container. Second fluid 30 is releasably retained within the container 26. Second container 26 also comprises at least one additional aperture 32 for releasing second fluid 30 from the container. Second container 26 is coupled to homogenizer 18 such that second fluid 30 is received by the homogenizer. Optionally, second container 26 is coupled to homogenizer 18 by a second tube 34. A gasket (not shown), which is optional, can be attached to the second container 26 at aperture 28, to second tube 34, or to homogenizer 18.

The containers can be fabricated from any material suitable in the art, including but not limited to plastic, glass, rubber, metal, ceramic, and the like. The containers can be transparent, translucent, opaque, or impenetrable to light. Gasket can be comprised of any material suitable in the art, including but not limited to elastomers such as silicon, and carbon-based elastomeric polymers, thermoplastic elastomers, nitrile butadiene rubber, butyl rubber, siloxanes, ethylene-propyldiene monomer, and the like.

Homogenizer 18 will function to produce a uniform desired particle size and desired slurry density, e.g., ratio of solid particulate matter to fluid. Homogenizer 18 can comprise at least one aperture 36 for receiving the solidified fluid 14 released from first container 10, and at least one aperture 38 for receiving the second fluid 30 released from second container 26. In some aspects, a single aperture can receive both the solidified fluid 14 released from first container 10, and the second fluid 30 released from container 26. Homogenizer 18 can comprise at least one aperture 40 for releasing two-phase coolant produced in the homogenizer. Optionally, third tube 42 can be coupled to homogenizer 18 via aperture 40. Third tube 42 can be used to deliver the coolant to a particular location such as those described and exemplified herein.

Optionally, the system may comprise a pump (not shown). The pump can be coupled to first container 10, second container 26, or homogenizer 18. Although forces such as gravity, and pressure released from container 10 can transport solidified first fluid 14 or second fluid 30 to homogenizer 18, in some aspects, it may be preferable to facilitate transport by use of a pump.

In the packaging process of the liquid into the first container, the container will be filled to a less than full volume. For example, filled with fluid to about one half of the total volume, although greater or lesser amounts of fluid are possible. The container can then be sealed, and attached to a gas cylinder about at the required pressure. Any suitable gas can be used to provide the pressure, including oxygen, carbon dioxide, nitrogen, or argon. The gas is then transferred to the first container to provide the required pressure. The amount of pressure can be varied to accommodate variables such as the type or volatility of the fluid, the fluid's atmospheric freezing point, and the like. Because the container is sealed, the pressure can be maintained at the desired level for an extended period of time. The pressure seal can be broken when the nozzle is opened to begin the spray.

The pressure from the first container can be used to provide the force for the flow to the homogenizer, and can be used to drive or entrain the fluid from the second container. If the containers are concentric, then the second fluid will be entrained by the velocity of the spray leaving the nozzle. In addition, the motion of the spray can optionally be varied to create a low pressure area, which in turn will siphon fluid from the second tank. A third option is to couple the pressure in the second tank to a nozzle outlet to increase pressure at the exit from the nozzle due to the expanding ice and gas. The pressure can then be harnessed to increase the pressure in the second container. The flow from the second container can travel under the nozzle, picking up micro-particulate ice on its path into the delivery system.

Also featured in accordance with exemplary aspects of the present invention are methods for producing coolants, including two-phase coolants. Generally, the methods comprise admixing a particlized solid with a carrier fluid. The particlized solid is preferably microparticalized and more preferably nanoparticalized, and is produced by releasing from a pressurized container a first fluid that has been cooled to a temperature below its atmospheric freezing point. It is preferable that the first fluid freezes into the solid substantially instantaneously. The freezing can proceed, for example, in an adiabatic manner. Any means suitable in the art, such as those described and exemplified herein, can be used to particalize the frozen fluid. The pressure in the container is maintained at a level to cause freezing point depression. The carrier fluid is also cooled to a temperature below the atmospheric freezing point of the first fluid. The mixing of the particlized frozen first fluid with the carrier fluid according to this aspect produces a slurry, i.e., a two-phase solution that can be used as a coolant in any suitable application, such as those described and exemplified herein. In some highly preferred aspects, the two-phase solution is homogenized to include a uniform particle size and/or uniform ratio of solid to fluid.

In some aspects, the first fluid and/or the carrier fluid is aqueous, or substantially aqueous. The aqueous fluid can be water, alcohol, or a physiologically compatible buffer such as, but not limited to, Hanks solution, Ringer's solution, or physiological saline buffer. The first fluid and/or carrier fluid can comprise at least one salt, monosaccharide, or polysaccharide, or a biomolecule such as nucleic acids, polypeptides, and lipids, or an analog, homolog, or derivative of any of the above. Any salt, monosaccharide, or polysaccharide known or suitable for the particular needs of the investigator can be used.

The first fluid and/or carrier fluid can comprise at least one emulsifier. Any emulsifier known or suitable for the particular needs of the application can be used. U.S. FDA-approved emulsifiers are highly preferred, particularly with respect to therapeutic or food-based applications of the resultant ice slurry. Some non-limiting examples of such emulsifiers include glycerol, soya oil, and egg lecithin.

The first fluid and/or carrier fluid can comprise at least one surfactant. Any surfactant known or suitable for the particular needs of the application can be used. U.S. FDA-approved surfactants are highly preferred. For example, families of surfactants made of Polyethylene Oxide (PEO) and Polypropylene Oxide (PPO), or Polyethylene Glycol (PEG) and Polypropylene Glycol (PPG) subunits are particularly preferred. These surfactants have been shown to be non-toxic, are generally regarded as safe, and have also been proven to be protective in cases of cell damage or micro-bubble embolization. Two families of surfactants are very highly preferred: the Poloxamer surfactants (PEG and PPG copolymer surfactants); and the Pluronic surfactants (PEO and PPO copolymer surfactants).

In some aspects, the first fluid and/or the carrier fluid is nonpolar, for example, an organic solvent. Any nonpolar fluid known or suitable for the needs of the application can be used. Non-limiting examples of these fluids include Perftoran, and perfluoro-x-anes, such as perfluorodecane and perfluorohexane. The two-phase coolant can comprise any ratio of solid to fluid suitable for the particular needs of the application. For example, the ratio may range from 0.001% solid to 99.999% solid and correspondingly 99.999% fluid to 0.001% fluid. At least about 10% solid void fraction in the fluid is preferred. More preferable is at least about 15% solid void fraction, more preferably at least about 20% solid void fraction, more preferably at least about 25% to solid void fraction, more preferably at least about 30% solid void fraction, more preferably at least about 35% solid void fraction, more preferably at least about 40% solid void fraction, more preferably at least about 45% solid void fraction, more preferably at least about 50% solid void fraction, and still more preferably at least about 55% solid void fraction can be used. At least about 60% solid void fraction in the fluid is even more preferred, and still higher percentages are even more preferred. Because it is preferred to maximize cooling in a given volume, it is highly desirable to provide the highest percentage of the solid void fraction as can be achieved given the materials chosen to comprise the resultant slurry. In some cases, chemical lubricants (emulsifiers and surfactants) and/or particle size controls can be used to enhance the level of solid void fraction.

The invention also features methods for using a coolant such as a two-phase coolant produced by the inventive systems and methods. The coolant can be used to cool or maintain a particular temperature in any application where lower temperatures or temperature maintenance is desired.

Thus, the invention provides methods for inducing or maintaining hypothermia in a subject. Such methods generally comprise administering to a subject in need thereof a pharmaceutically acceptable coolant such as a two-phase coolant produced according to any of the inventive methods described or exemplified herein. The coolant is administered to the subject in an amount effective to induce hypothermia. The effective amount may be dependent on various factors that are expected to be known in the art. Non-limiting examples of such factors include the species, height, weight, age of the subject, and the like. Administration can proceed by any means suitable for the particular application to which the coolant is being used. For example, the coolant can be administered intravenously, intramuscularly, intraperitoneally, topically, orally, nasopharyngeally, anally, vaginally, into the thoracic cavity, into the lungs, into other corporeal spaces, regions, and the like. Intravenous administration is highly preferred.

The methods can be used in any subject. Preferably, the methods are used in mammals such as horses, cows, pigs, dogs, cats, rabbits, rats, hamsters, and mice. The methods are preferably beneficially employed in humans.

The hypothermia can be systemic, meaning that hypothermia can be induced and/or maintained throughout the entire body of the subject. Alternatively, the hypothermia can be directed to a particular location or locations of the body, for example, to a particular organ, appendage, cavity, space, or region.

Also provided are methods for rapidly cooling or maintaining a cool temperature for perishable goods. Such methods generally comprise producing a coolant such as a two-phase coolant according to any of the inventive methods described or exemplified herein, and exposing the perishable goods to the coolant. Perishable goods refers to any product, compound, or composition that has a finite shelf life. Non-limiting examples of perishable goods include food products such as meats, fish, produce, milk and milk products, confectionaries, beverages, and the like, pharmaceuticals, vitamins, minerals, is volatile chemicals, radionuclides, biomolecules such as nucleic acids, polypeptides, and lipids, cells, tissues, organs, and biological fluids such as blood, blood serum, urine, saliva, sweat, milk, and the like.

Also featured are methods for rapidly cooling heat generating devices such as a weapon or high powered electronics. The methods generally comprise producing a coolant such as a two-phase coolant according to any of the inventive methods described or exemplified herein, and exposing the weapon to the coolant. Any weapon or sub-part of a weapon such as a gun barrel can be cooled using the inventive method. Non-limiting examples of suitable weapons include guns, cannons, and electromagnetic pulse generators. Weaponized lasers can also be cooled according to the inventive methods. The weapons can be hand-held, or those attached to equipment such as a plane, helicopter, or vehicle. Non-limiting examples of high powered electronics are computers, appliances, micro-electronic devices, power transformers, and the like.

The invention also features methods for cooling a room. The methods generally comprise producing a coolant such as a two-phase coolant according to any of the inventive methods described or exemplified herein, exposing air to the coolant such that the temperature of the air is lowered, and circulating the cooled air throughout the room. The air can be exposed to the coolant according to any means suitable in the art. Similarly, the cooled air can be circulated according to any means suitable in the art, such as a fan. The invention contemplates that multiple rooms can simultaneously be cooled through the inventive methods. For example, through appropriate duct work, the cooled air can be circulated to multiple rooms, including all rooms of a particular building, at the same time.

The invention also features methods for non-lethal crowd control. The high volume and pressure pumping of the two phase coolant, for example, out of a water cannon can be used to disperse rioting crowds through the creation of severe discomfort through the rapid cooling caused by full body exposure to the two phase coolant.

The invention also features a method for improvement of fire control or suppression methods. The high volume and pressure pumping of the two phase coolant out of, for example, a fire hose may improve fire fighting procedures as the environmentally friendly two phase coolant can draw more heat out of the fire, reducing the energy of the combustion process, making the fire easier to control and suppress. Additionally the release of ice slurry from fire sprinkler systems can have the same effect on the fire.

The invention also features methods for the protection of structural elements during extreme heat. Non-limiting examples of extreme heat are: a building fire, space craft atmosphere re-entry, or metal foundry equipment. In extreme heat events, the heat can exceed the limits of the structural members, resulting in building collapse, space craft disintegration, or failure of mechanical systems. If members of these systems were designed in conjunction with a high volume two phase coolant production system to provide integrated heat transfer conduits, the members may be cooled directly during the heating event, lengthening the time to structural failure.

Additionally the invention features methods for personal cooling systems. Personal cooling may improve personal performance during physical activity or otherwise help prevent corporeal over-heating. Non-limiting examples of personal cooling systems are personal misters, bench misters for sports teams, body cooling systems as may be worn under other clothing, equipment, helmets, gloves, shoes, and the like to cool the desired portion of the body.

Additionally the invention features methods for the removal or safe handling of toxic gases. As a liquid's temperature is reduced, the amount of gas that can be dissolved in the liquid increases. The described methods may be used to create a two phase air scrubbing liquid. This liquid can then be used to quickly filter air that has been exposed to any of a variety of toxic gasses, non-limiting examples of which are, carbon monoxide, poison gas, radio-active gas, radio-active particulate, asbestos particulate, and the like. An alternative aspect of the same device can allow for the safe handling of weapons that contained such gases.

Additionally the invention features methods to rapidly induce deep hypothermia for the induction of a cryostasis state. This method may be employed for medical benefit in hospitals, or alternatively may be employed to induce stasis for long term space travel. The location of the deep hypothermia induction may require different embodiments of the two phase coolant production system. Systems designed for use in space may use the vacuum of space as its primary coolant.

In any of the above-described methods, or other methods to which the invention can be adapted, the rate of cooling can be controlled. Cooling can thus proceed slowly or rapidly, at a uniform rate, or at a staggered rate, for example, rapidly for a period of time, followed by a slow period. The rate of cooling can be determined and adjusted according to the particular needs of the application. The rate of cooling can be controlled according to any means suitable in the art. Suitable methods for controlling the rate of cooling include, but are not limited to, adjusting the delivery rate of the slurry or adjusting the ice content of the slurry. The method used to control these parameters can depend on the particular configuration of the device, but can include changing the pumping rate, or the percentage that a valve or nozzle is open. It is contemplated that cooling systems provided by this invention can advantageously be used for a large variety of additional applications. Some non-limiting examples of such applications include storage, shipping, and air conditioning in various industries. Additional applications can be found, for example, in the health care industry, where cooling of patients is gaining recognition as a therapy to improve outcomes for trauma, cardiac arrest, ischemic injury and the like. Cooling is also advantageous for devices that generate excess levels of heat that could damage components of the device. Such devices include computers, weapons, tools, motors, vehicles, and the like.

Refrigerant chemicals or machines are optionally used to generate cold air or ice in some applications. But because many refrigerant chemicals such as chlorofluorocarbons are toxic and can potentially damage the environment, such cooling systems are less preferred than those embodiments described herein that can be operated without the use of refrigerant chemicals. Similarly, because many commercial air conditioning or refrigeration units can use large amounts of energy, potentially taxing energy grids during peak demand, such cooling systems are less preferred than those embodiments described herein that can be operated without the use of large amounts of energy.

Two-phase, solid-liquid coolants of the type described herein can be beneficially employed for a variety of uses, including medical, refrigeration, and HVAC applications, crowd control, and fire suppression, among others. In some applications, it is particularly beneficial to verify the quality, i.e., cooling capacity, of such coolants at the site of action where the coolant is applied. A quality assurance system that will allow the reliable use of two-phase coolant systems in various applications is therefore desirable.

Cooling capacity in two-phase, solid-liquid coolants correlates to the void fraction and particle size of the coolant solids. Particle detection devices employing ultrasound or light scattering are optionally used to make measurements for determining cooling capacity. In applications in which significant power and computational requirements may not be available, or in which a clean, stable environment may not be available, it is beneficial to have a quality assurance system with minimal power and computational demands that can be scaled for different applications in unpredictable environments, such as battlefield, emergency, or marine settings.

Figure 2:
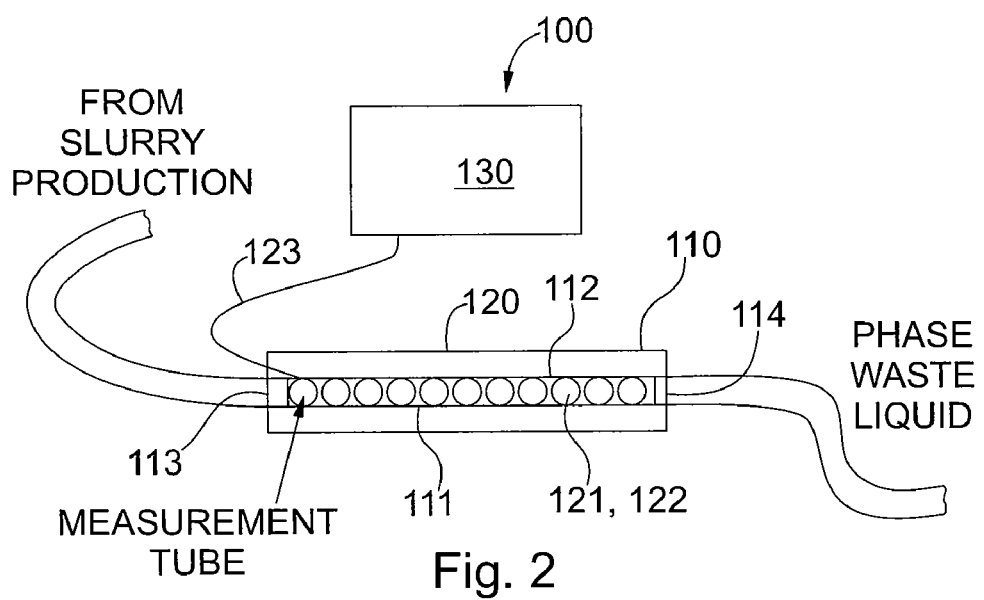
FIG. 2 shows a schematic diagram of an exemplary embodiment of a system to measure solid void fraction and particle size in a two-phase, liquid-solid coolant.

As shown in FIG. 2, in a preferred embodiment a system 100 for determining the cooling capacity of a two-phase, solid-liquid coolant is provided, including a conduit 110 having an interior 111 and an exterior 112, a predetermined length, and known heat transfer characteristics. The conduit can be made from a metal such as copper, aluminum, or stainless steel. The conduit can be rifled to cause laminar mixing of the coolant as it travels through the quality measuring device. The internal dimension of the rifled conduit device can be of the same dimension as the entry and exit tube, which can vary based on the application. By way of example but not of limitation, a gastrointestinal delivery system can have a larger conduit than an intravenous delivery system. The external diameter of the conduit preferably will not exceed twice the inner diameter. The conduit 110 further has an inlet 113 and an outlet 114 adapted respectively to receive and discharge a predetermined volumetric flow of coolant, which flows through the interior 111 of the conduit 110. A heat source 120 is positioned relative to the conduit 110 to transfer heat to the coolant flowing through the conduit interior 111. The heat source for the device optimally can be provided in the form of a series of resistive thermal devices (RTD) powered with an electric current. The RTDs can be micro-fabricated into the wall of the conduit, or can be attached to the interior or exterior of the conduit as well. The RTDs can be controlled so that a constant temperature is maintained. In addition the RTD can have built-in heat flux and temperature sensors. At least one heat flux sensor 121 and at least one temperature sensor 122 are positioned on the conduit 110. Sensor wires 123 connect the sensors 121 and 122 with an electronics element 130, typically a computer or other semiconductor device.

In operation, a predetermined volumetric flow of a two-phase, solid-liquid coolant, preferably an aqueous slurry of ice, is drawn from the output of a coolant delivery system and directed to the inlet 113 of the conduit 110. Preferably, the coolant flow to the conduit 110 is drawn from a source as near as possible to the point of application of the coolant so that the cooling capacity of the coolant at the application point is determined. Heat is transferred by the heat source 120 to the coolant flowing within the conduit interior 111. The exterior 112 of the conduit 110 preferably is maintained at a constant temperature. It is also preferable that a substantially uniform cross-sectional distribution of solid and phases in the coolant is maintained as the coolant passes through the conduit 110. Rifling or vanes can be present in the conduit to induce mixing to ensure homogeneity of the fluid.

The heat flux and temperature sensors 121, 122 measure heat transfer and coolant temperature as functions of the distance the coolant travels within the conduit interior 111.

Figure 3:
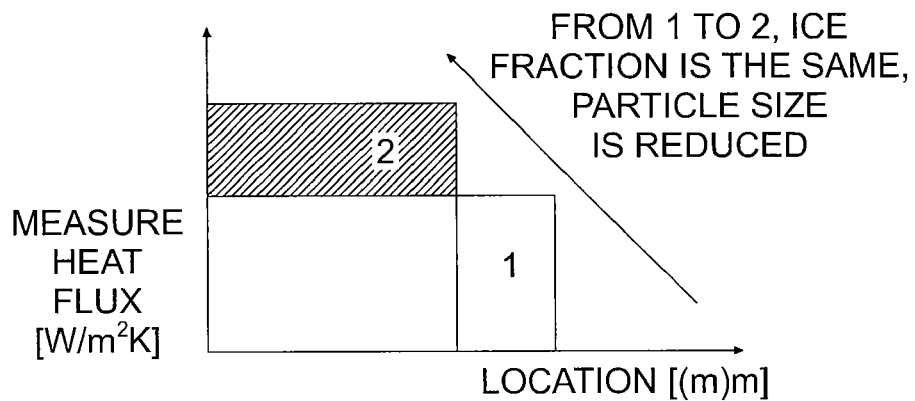
FIG. 3 shows a graphic diagram of the effect of particle size on heat flux measurement.

Signals are transmitted through the sensor wires 123 from the sensors 121, 122 to the electronics element 130, such as a computer. The electronics element 130 is provided with correlations of the measured heat flux to the coolant and coolant temperature with coolant properties, including cooling capacity, solids void fraction, and solids particle size. Using the measured heat flux and temperature values, the electronics element calculates the relevant coolant properties. As shown in FIG. 3, decreasing solid particle size correlates to an increase in measured heat flux.

Also featured in accordance with the present invention are systems and methods for portable on-demand production of a two-phase coolant. One obstacle to providing rapid cooling, for example, to induce therapeutic hypothermia in the field is finding a power source large enough to cool liquids such as a saline solution to form ice in the short time span that is available to treat a patient. In addition, in the therapeutic setting, this power need is complicated by the fact that cooling of the patient ideally begins outside of the hospital, meaning that the large power source needs to be available on emergency vehicles.

By way of example, for two liters of aqueous saline to be cooled from about room temperature to the freezing point, approximately 0° C., with one of the two liters needing to be frozen to ice, the total energy required would be about 550 kilo-joules. To carry out this process in about 5 minutes would require more than 1.8 kilo-watts of energy, assuming ideal conditions. Refrigeration units that provide that type of cooling power are available, but generally require special 220 volt wiring and are generally large and heavy, weighing hundreds of pounds. Moreover, as conditions are often not ideal, it is likely that these estimated power needs represent a significant under-estimation of the actual power that would be required. Thus, the requisite refrigeration units in reality are likely to be even heavier and require more power to operate. The size and power requirement limitations would limit the ability to produce a two phase coolant in an emergent setting in a hospital building, and severely limit, if not prohibit the ability to produce such coolants from an emergency vehicle within the time constraints of a medical emergency.

To overcome such limitations, one possible solution can be to create the two phase coolant before it is needed, and to store it. Advance preparation could significantly reduce the flow rates of the coolant, thereby reducing the power consumption. Two phase coolants such as slurry lose their preferred ice particle shape and pumpability characteristics, however, upon storage, thereby reducing the therapeutic value of the coolant. An aqueous ice slurry is in a constant state of phase change between the ice and liquid forms of water. Over time, the dendritic nature of the ice crystals is restored and the slurry would no longer be able to be moved, even pumped, within the tight constraints of, for example, an intravenous tube.

Figure 5:
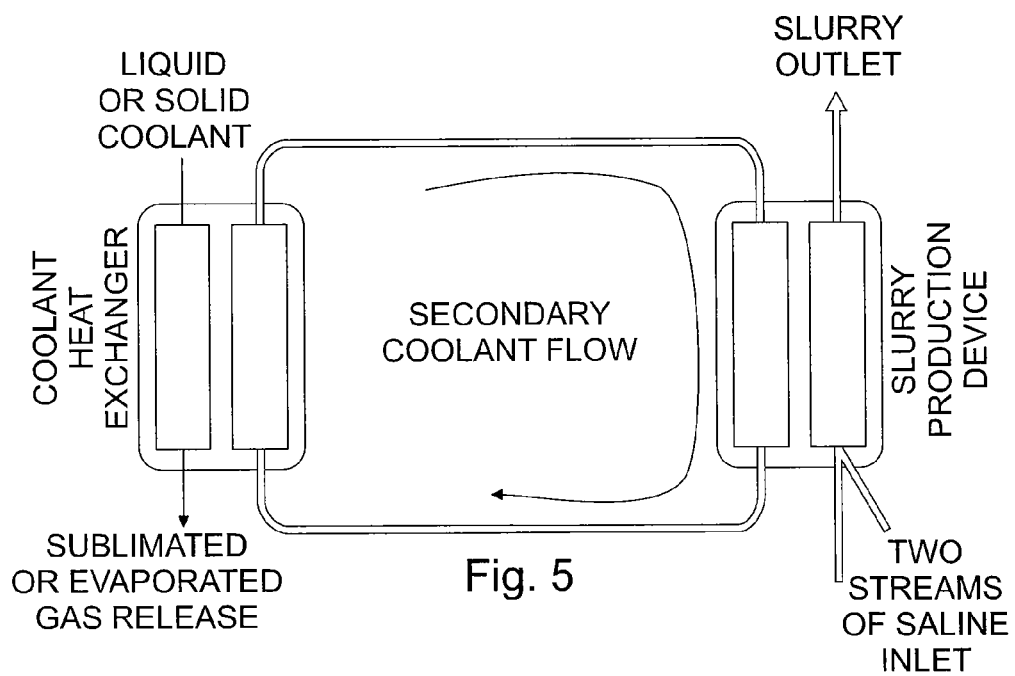
FIG. 5 shows a schematic of an embodiment of a two phase coolant production system that utilizes phase changes as opposed to electrical refrigeration to promote freezing.

It has been discovered in accordance with the present invention that the stored thermodynamic energy of, for example, compressed gasses or dry-ice, can be harnessed for the portable on-demand production of two phase coolant. However, such use of thermodynamic energy for cooling liquids creates temperatures below the eutectic point of salt water, which results in an ice slurry having a temperature much lower than 0° C., which could be harmful to a patient. This challenge was overcome by the discovery that use of one or more heat exchangers can control the freezing temperature of the aqueous saline. The use of heat exchangers provides the additional advantage of also allowing for the use of stored cooling in the form of dry-ice sublimation, or liquid evaporation. An overview of the use of heat exchangers is illustrated in FIG. 5. More details of embodiments of the inventive systems are provided below with reference to FIGS. 6-14.

The pressure drop, heat flow, and mass flow rates of the heat exchanger can be modified by scaling its linear dimensions. The skilled artisan can, for example, consult the introductory chapter of John E Hesselgreaves' Compact Heat Exchangers: Selection, Design and Operation (Elsevier Science Ltd. 2001) for guidance in this regard. Any dimensions of devices described or exemplified herein are intended to be illustrative, and not limiting. Accordingly, dimensions can vary, for example, according to the particular system, device, application, or needs of a particular user or investigator.

In one aspect, the two phase coolant productions systems utilize medical grade saline solutions, which generally contain from about 0.45% to about 7.5% solute, to create a sterile ice-saline slurry on demand for inducing hypothermia in a patient. For example, the sterile ice slurry produced can be used to quickly induce therapeutic hypothermia for patient protection during sudden death, heart attack, stroke, heat stroke, septic shock, hemorrhagic shock or any medical condition wherein uncontrolled metabolic injury is a concern.

Figures 6A, 6B:
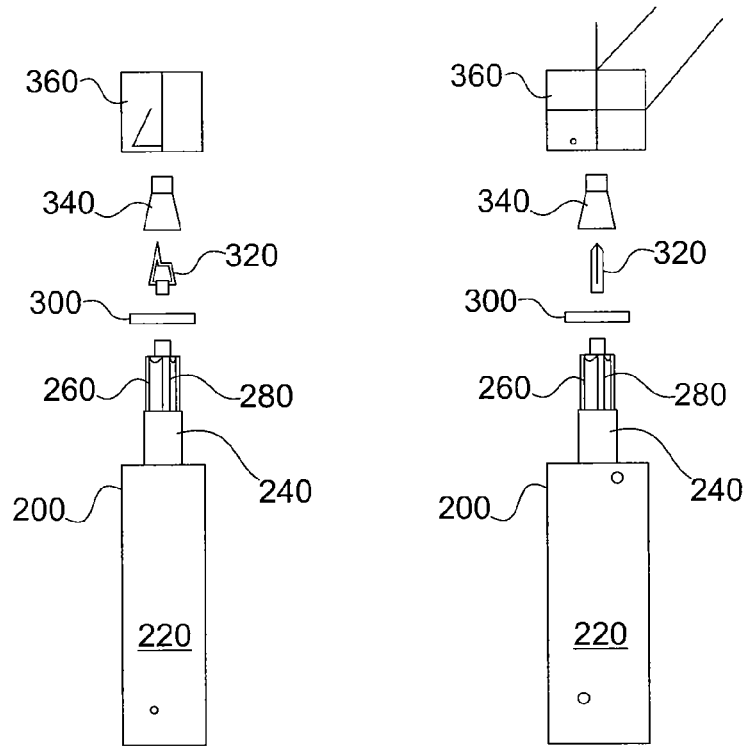
FIG. 6A-B shows an exploded view of one embodiment of a two phase coolant production device.

As shown in FIG. 6A-B, two phase coolant production systems can comprise several principle component parts assembled into a slurry production device 200. An exploded view of an example of a suitable assembly configuration is provided. FIG. 6B shows a 90 degree rotation of the configuration shown in FIG. 6A. The figure shows a housing 220, heat exchanger 240, driveshaft 260, ice scraper blade 280, internal disk 300, mixing blade 320, mixing vessel 340, and a mixing vessel housing 360. The assembly can further comprise gaskets and connectors such as screws or snap fits (not shown).

Figure 7A:
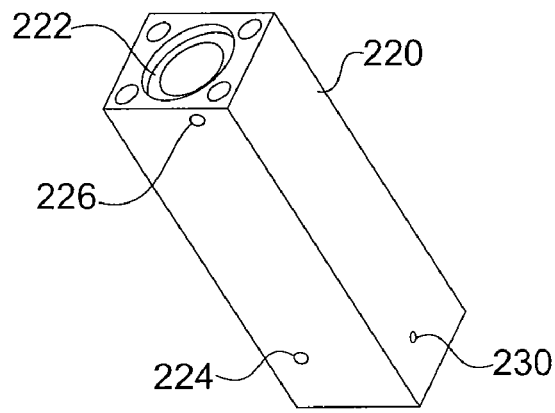
FIG. 7A-B shows an embodiment of a housing for the various components of a two phase coolant production device.
Figure 7B:
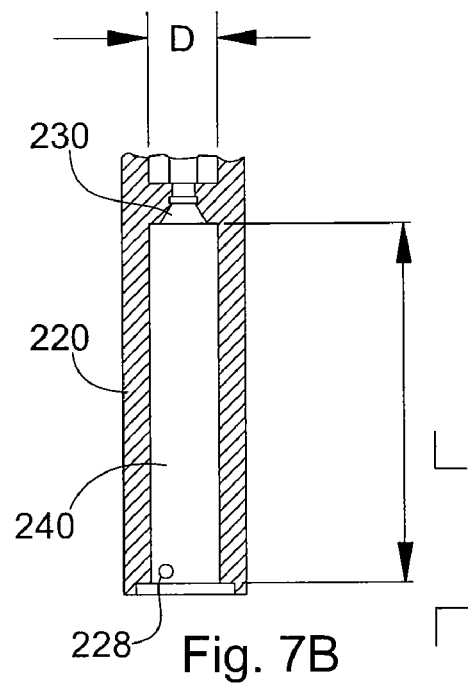

In some aspects, the systems comprise a housing 220 configured to contain the principle components of the two phase coolant production system. The housing can be comprised of any suitable material such as metal, plastic, rubber, silica, polymers, glass, wood, and the like. The housing can be insulated. Plastic is a preferred material. As shown in FIG. 7, the housing can comprise a lumen 222 for containing the components of the two phase coolant production system. FIG. 7A shows one exemplary exterior configuration of the housing. FIG. 7B shows a cut-away view of the housing, showing an example of a configuration of additional components of the slurry production system within the housing. The components can be fastened to the housing according to any means suitable in the art. Preferably, the components are reversibly assembled to allow the components to be periodically cleaned and/or sterilized.

The housing can also comprise apertures, which can be used, for example as a coolant inlet 226 and a coolant outlet 224, as well as an inlet 230 for fluid that is to be frozen into the ice component of a resultant ice slurry and an outlet 228 for the ice is slurry. The apertures can optionally comprise connectors configured for connecting the housing to fluid containers, slurry storage containers, tubing for delivery of the slurry, additional components of the system, and the like. Connectors can be any connector suitable in the art for the purpose to which it is being used.

The housing preferably comprises a heat exchanger 240. The heat exchanger can comprise a length L and a diameter D (FIG. 7B). In some preferred aspects, the heat exchanger can comprise one or more tubes, preferably concentric tubes, that separate the coolant from the fluids that comprise the two phase coolant.

Figure 8:
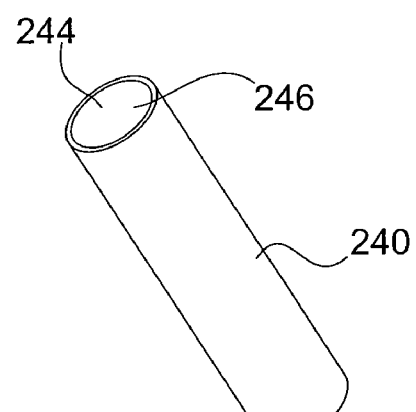
FIG. 8 shows an embodiment of a heat exchanger that can be used in the coolant production assembly shown in FIG. 6.

As shown in FIG. 8, the heat exchanger 240 can comprise one tube. The tube has a lumen 244 through which the fluids that comprise the two phase coolant can flow, and the ice phase of the slurry being produced can be formed on the sidewalls 246 of the lumen. The coolant flows between the housing 220 and the heat exchanger tube 240. The heat exchanger tubes can range in length from about 1 inch to about 24 inches, although shorter or longer tubes can be used. Preferably, the tubes are about 1 inch to about 6 inches long. The inner tube can range in diameter from about 0.25 inches to about 2 inches. Preferably, the inner tube diameter is about 0.5 inches. The outer tube can range in diameter from about 0.5 inches to about 2.5 inches. Preferably, the outer tube diameter is about 0.8 inches. In one non-limiting example of a single heat exchange tube, tube length L is about 6 inches and diameter D is about 0.75 inches.

The heat exchanger tubes can be fabricated from any material suitable in the art, and the material chosen may depend on the use to which the system is being put. The heat exchanger tube can comprise a metal such as stainless steel, platinum, or titanium. Preferably, the heat exchanger material is stainless steel. The inner and outer tubes can be comprised of the same material or different materials. The outer tube can be comprised of stainless steel, platinum, titanium, Nylon, polycarbonate, Teflon, or Tygon. Preferably, the material is insulating and sterilizable, such as polycarbonate.

The heat exchanger tube is contained within the housing, and the walls of the heat exchanger tube are directly contacted with the coolant flowing through or otherwise present in the housing lumen. The tube can be fastened to the housing, or can be free floating within the housing. The coolant cools the heat exchanger tube to a temperature sufficient to freeze the fluid that contacts the sidewalls of the heat exchanger tube. In addition, the cooling of the fluid can result in the freezing of fluid not in direct contact with the heat exchanger tube sidewalls. The coolant can be any coolant suitable in the art for freezing the fluid of interest. Non-limiting examples of coolant include dry ice-alcohol slurry, compressed refrigerant gases such as Freon and ammonia, polyethylene glycol, polypropylene glycol, water, freezing point depressed water such as sodium chloride saline or potassium formate saline or dextrose solutions, alcohols, and the like.

Figure 9:
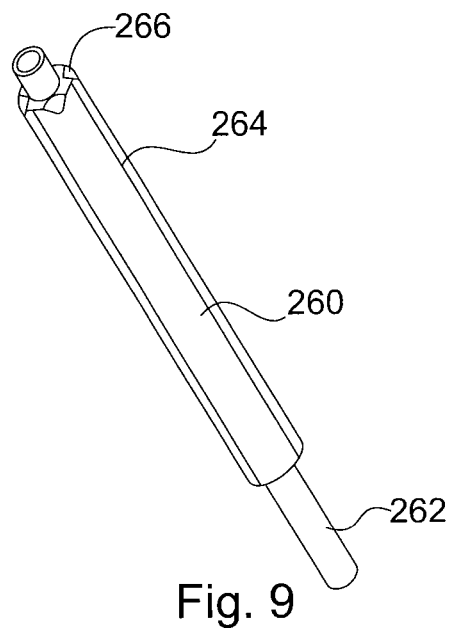
FIG. 9 shows an embodiment of a driveshaft that can be used in the coolant production assembly shown in FIG. 6.

The tube of the heat exchanger preferably comprises a driveshaft 260, for example, as shown in FIG. 9. The driveshaft can comprise an axel 262 to allow the driveshaft to rotate within the heat exchanger inner tube. The driveshaft can further comprise one or more scraper blade holders 264 to reversibly fasten one or more scraper blades to the driveshaft. The drive shaft can further comprise one or more channels 266 to facilitate the flow and transport of fluid and the forming ice slurry through the heat exchanger. The channels can be cut into the distal end of the driveshaft at an angle to provide pulsatile flow through downstream components of the slurry production assembly. One of the challenges of creating a coolant of this type is the propensity of the ice particles to aggregate and coalesce, ruining the pumpability of the slurry. Blunt obstructions in the slurry flow path provide flow stagnation points, which in turn provide locations for ice particle aggregation. Pulsatile flow can help reduce or even eliminate any ice particle jamming that is likely to occur with the dendritic ice crystals. In addition, the driveshaft provides appropriate means of connection with the mixing blade 268.

The driveshaft can be fastened to the heat exchanger or to the housing. The driveshaft can rotate clockwise, counterclockwise, or in combinations thereof. The driveshaft can rotate at any speed suitable in the art. The driveshaft rotation speed can be correlated to the number of ice scraping blades. For example, from analysis of the water freezing process, it was determined that the ice interface can preferably be scraped from about every thirtieth to about every fifth of a second. In some preferred aspects, the ice interface is scraped every twentieth of a second. Therefore, a driveshaft having one scraping blade can preferably rotate at about 1200 rpm. A driveshaft with two scraping blades can preferably rotate at about 600 rpm. A driveshaft with three scraping blades can preferably rotate at about 400 rpm. A driveshaft with four scraping blades can preferably rotate at about 300 rpm. This relationship between number of scraping blades and the rpm of the driveshaft can continue to any number of scraping blades. In more preferred aspects, the driveshaft rotates from about 0.0001 to about 200 rpm. Rotation can be effectuated according to any means suitable in the art, including the use of a motor. In some embodiments, a battery or AC powered motor of appropriate power can be attached to the proximal end of the driveshaft 262. In other embodiments, a turbine blade can be attached to the proximal end of the driveshaft 262. This driveshaft can be powered by a pump that is used to pump fluid through the device.

Figure 10:
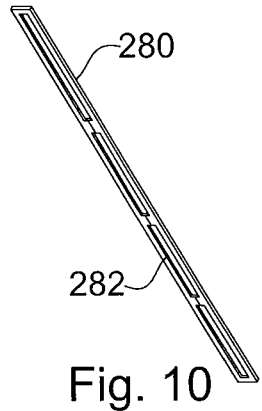
FIG. 10 shows an embodiment of an ice scraper blade that can be used in the coolant production assembly shown in FIG. 6.

The driveshaft can comprise one or more scraper blades 280, as illustrated in FIG. 10. The scraper blades are configured to remove the formed ice from the sidewalls of the inner tube. Each scraper blade can optionally comprise one or more apertures 282. The apertures can allow for the scraped ice particles to pass freely through the scraper blade. The apertures can range in size from about 1/16 inch to about 1/2 inch wide and from about 1/4 inch to about 8 inches long. Preferably, the apertures are about 1/8 inch wide and 3/4 inch long.

Free passage through the scraper blade can help to ensure homogeneity of the resultant slurry. The scraper blade can be comprised of any material suitable in the art, including metal, plastic, rubber, glass, polymers, silica, and the like. The ends of the scraper blades that contact the ice formed on the sidewalls of the inner tube can be tapered. The scraper blades can be configured as an auger. In the auger configuration, the scraper blades serve at least two purposes. In one aspect, the auger blades can serve to scrape the ice off of the heat exchange interface and can be used to transport the saline slurry through the device. The auger embodiment can advantageously require fewer pumps, and thus less electrical power to operate. The number of auger scraper blades can vary from one to many. The number of blades can be determined according to different variables, including by relating the desired slurry flow rate, the auger parameters (lead, lead angle, and mean auger diameter), and the desired RPM of the motor.

Figure 11B:
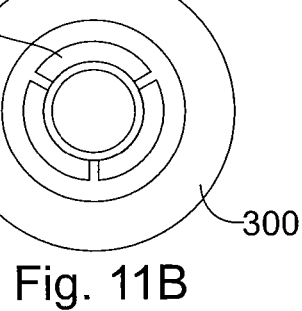
FIG. 11A-C shows an embodiment of an internal disk that can be used in the coolant production assembly shown in FIG. 6.
Figure 11A:
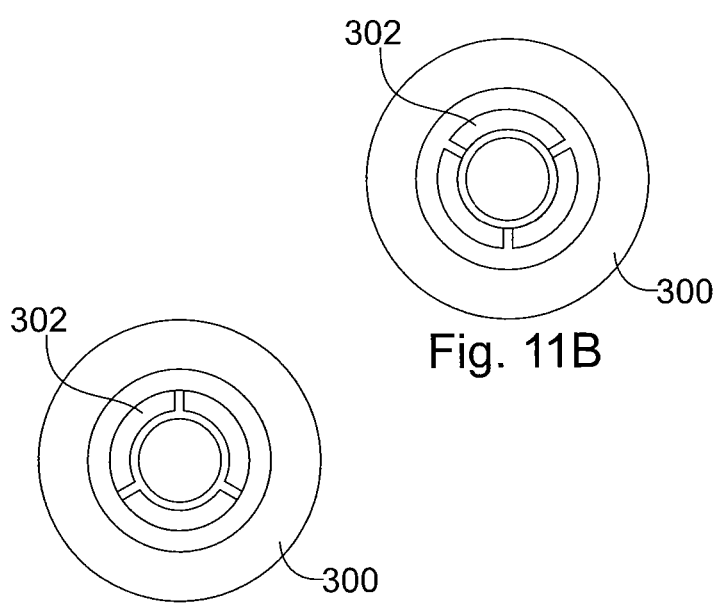
Figure 11C:
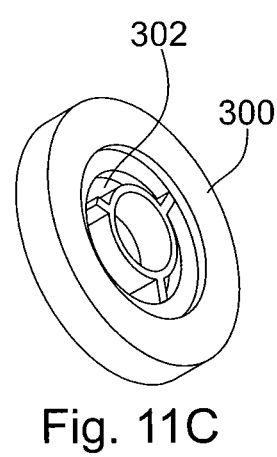

In some aspects, a slurry production assembly can comprise an internal disk 300, as shown in FIG. 11A-C. Figures A-C show different view angles of the internal disk. The internal disk can hold the bearing near the end of the driveshaft. The internal disk can comprise one or more apertures 302 to allow the produced ice-saline slurry to pass through the disk to subsequent components of the device. In addition, the disk comprises two faces for compressive forces to seal the device together, comprises the distal end of the heat exchanger, and comprises the proximal end of the mixing vessel. Optionally, gaskets can be used between the distal end of the heat exchanger and the disk, and between the proximal end of the mixing vessel and the disk.

Figure 12A:
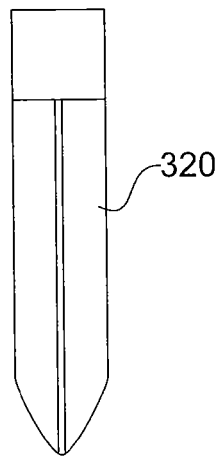
FIG. 12A-C shows an embodiment of a two phase coolant mixing blade that can be used in the coolant production assembly shown in FIG. 6.
Figure 12B:
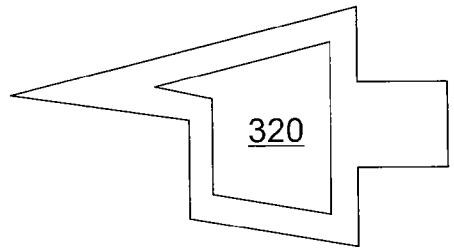
Figure 12C:
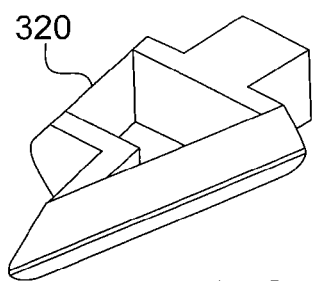

The slurry production assembly comprises, in some aspects, a mixing blade 320. One non-limiting example of a mixing blade configuration is shown in FIG. 12A-C. FIG. 12A shows a side-view of the mixing blade, FIG. 12B shows a top-view of the mixing blade, and FIG. 12C shows a three-dimensional perspective of the whole mixing blade. This blade is configured to mix and/or finely homogenize the ice slurry produced in the heat exchanger, which will be dendritic ice slurry, and a high concentration saline. The blade shape can be designed to create turbulent (chaotic) mixing of the slurry and the high concentration saline. In some aspects, the mixing blade is configured to push the slurry out radially, in turn forcing the high concentration saline into the more central volume.

The ice particles initially formed to comprise the ice slurry generally comprise sharp, dendrite-like edges. The shape of the formed ice can impede or even prevent transport pumping of the slurry through tubes, for example, for delivery to a patient. It has been discovered that smoothing of the ice particle shape, which can occur in either the primary ice formation process or in a secondary smoothing process can overcome the problems of transporting ice slurry comprising dendritic ice crystals. This described secondary process could be added to many commercially available slush production devices making the slurry more pumpable or drinkable. Non-limiting examples of currently available slush production devices are: the ORS-1075HS HUSH-SLUSH® (O.R. Solutions, Inc., Chantilly, Va.) system, SLURPEE® machines (7-Eleven), slushie machines, frozen alcoholic beverage machines, systems for building refrigeration using two phase coolants, and the like.

It has further been discovered that smoothing of ice particle shape can be effectuated by controlled heating of the ice slurry, by addition of an effective amount of a high concentration saline to the slurry, or by addition of an effective amount of a non-frozen liquid. The addition of a small amount of heat to the slurry, which can occur by heat flux or liquid flux, while the slurry is being agitated can lead to the development of smooth ice particles. The amount of heating required can depend, for example, on the desired flow rate of the slurry. The heat can be added by maintaining a wall temperature higher than the slurry average temperature. Non-limiting wall temperatures can range from about 0° to about 40° Celsius., with both the low range 0-4 degrees Celsius and 30-40 degrees being preferred. The two preferred temperature ranges correspond to differing heating areas, with the larger heating area corresponding to the lower wall temperature.

The high concentration saline can comprise from about 1 to about 10 percent solute, including commercially available 3.5%, 5%, and 7.5% medical grade saline. The saline can comprise one or more of the following non-limiting solutes, which are preferably pharmaceutically acceptable or physiological salts or sugars, non-limiting examples of which include: sodium chloride, sodium lactate, potassium phosphate, calcium chloride, potassium chloride, sodium phosphate, potassium diphosphate, potassium formate, glucose, and dextrose.

Figure 13:
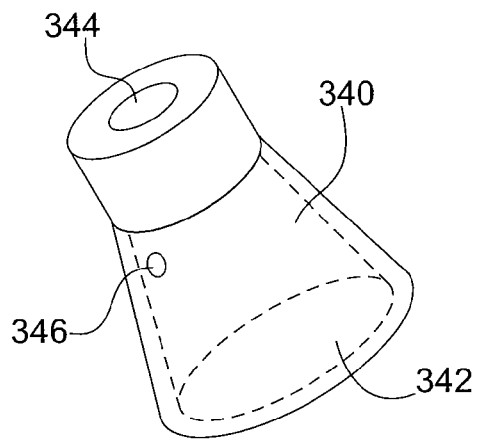
FIG. 13 shows an embodiment of a mixing vessel that can be used in the coolant production assembly shown in FIG. 6.

Controlled heating of the ice slurry and/or the addition of a high concentration saline to the ice slurry can be effectuated in any component of the slurry production assembly. In one preferred aspect, the assembly comprises a dedicated component for smoothing of the ice particles, for example, a mixing vessel. The mixing vessel can be configured according to any shape and size suitable in the art. In one highly preferred aspect, the mixing vessel is cone-shaped, as shown in FIG. 13.

A mixing vessel 340 can comprise an inlet 342 for ice slurry formed in the heat exchanger that passes through the internal disk. The mixing vessel can also comprise an outlet 344 for effluent of the refined slurry, for example, to be administered to a patient. In some aspects, the vessel can comprise an inlet 346 or a plurality of inlets to allow for the addition of high concentration saline to the vessel lumen. The mixing vessel can house the mixing blade. In some aspect the vessel can be heated to smooth the shape of the ice crystals. Non-limiting examples of methods to heat the mixing vessel include incorporating thermal resistive devices into the mixing vessel wall, passing a warm fluid around the exterior of the mixing vessel wall, or having the mixing vessel wall be comprised of a heat pipe, wherein the heat pipe could provide a set wall temperature higher than the slurry temperature. The vessel can be manufactured from any material suitable in the art, such as metal, plastic, rubber, silica, polymers, glass, and the like, and can optionally be insulated.

Figure 14:
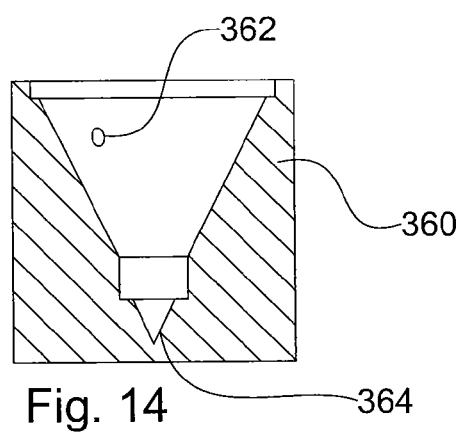
FIG. 14 shows an embodiment of a mixing vessel housing that can be used in the coolant production assembly shown in FIG. 6.

In some embodiments, the slurry production assembly can comprise a mixing vessel housing 360. An example of a vessel housing configured to contain a mixing cone is shown in FIG. 14. The vessel housing component can be configured to hold components of the assembly on the distal side of the internal disk, and can be reversibly fastened to the main housing of the assembly, providing the compression that seals all of the different compartments and holds the entire assembly together. In some preferred aspects, the vessel housing comprises one or more apertures 362 to allow the high concentration slurry to pass through the vessel housing and into the mixing vessel. In some preferred aspects, the vessel housing comprises one or more outlets 364 for the effluent of the produced slurry from the slurry production assembly. In some highly preferred aspects, the outlet can comprise a fitting 366 for connection to a tube such as an intravenous tube, for administration of the slurry to a patient. Any fitting suitable in the art can be used, such as an IV luer connector. Other non-limiting possible connectors include: standard plumbing connectors for use with building cooling, perishable goods cooling, or fire suppression sprinkler systems, connectors appropriate for cooling of weapons such as lasers, guns, cannons, and electro-magnetic pulse generators, connectors appropriate for fire hoses and water cannons, connectors appropriate for personal cooling systems such as cooling caps, cooling vests or personal mister systems, connectors appropriate for personnel misting systems (sports team benches), connectors appropriate for cryogenic stasis systems, connectors appropriate for cooling of foundry equipment, connectors appropriate for structural element cooling under extreme conditions such as building frame cooling during fire or space craft protection during damaged heat shield re-entry, connectors appropriate for air scrubbing systems, connectors appropriate for improved toxic gas containment and transport, connectors appropriate for minimally invasive surgical instruments for use in organ preservation during prolonged surgeries, connectors appropriate for storage tank deposition, connectors appropriate for localized medical cooling such as a gastro intestinal tube, or tubing for lung lavage or tubing for slurry emission into the nasopharyngeal, oral, aural, anal or vaginal cavities, connectors appropriate for slurry emission into intraperitoneal or intrathoracic spaces, or connectors appropriate for emission into any other physiological is space or region.

In some aspects, the slurry production system, such as the assemblies described and exemplified herein, comprise four volumes. The first volume contains low concentration saline and is cooled so that ice forms in the saline. In some preferred aspects, the slurry can comprise from about 10 to about 90% ice, although higher or lower percentages can be produced, depending on, among other things, the particular needs of the investigator. More preferably, the slurry comprises from about 20 to about 80% ice, more preferably from about 30 to about 70% ice, more preferably from about 40 to about 60% ice, and more preferably from about 50 to about 60% ice.

The second volume can surround the first volume and can be separated by the configuration of the heat exchanger. This second volume is where the coolant is re-circulated. Preferably, the coolant and the saline have opposite flow directions to create a counter-current heat exchanger. The coolant can be circulated through a phase change refrigeration unit where the heat is removed. Preferably, the refrigeration unit is non-electrical, but can also be electrical.

The third volume is where the ice slurry produced from the heat exchanger is heated or mixed with the high concentration saline. Controlled heating or mixing of the ice particles with additional salt smoothes the ice particles can make the slurry pumpable. The mixing blade can be present in the third volume.

The fourth volume can surround the third volume and is where the high concentration saline is introduced into the assembly. The volume is configured to allow the high concentration saline to flow freely to all surfaces of the mixing vessel. This facilitates uniform mixing, and also reduces drag as the ice slurry flows through the vessel. The completed ice slurry travels out of the end of the vessel. In some aspects, the slurry can be pumped through one or more of the components of the assembly, and/or it can be pumped through a tube for administration to a patient.

In a counter current heat exchanger configuration, coolant flow rate and saline flow rate can be physically related based on the void fraction of ice that is desired. In addition, heat transfer equations can be complicated by changing temperatures in the heat exchanger wall as a function of distance through the device. In addition, energy may be required to pump the coolant liquid. To optimize configuration and operation of a slurry production system, it has been discovered that annular heat pipes can be used as a heat exchanger in the system. Accordingly, in some preferred aspects, the heat exchanger can be a heat pipe, preferably an annular heat pipe.

According to an exemplary embodiment, a heat pipe is essentially a self contained, surface tension driven, heat pump. When a temperature gradient is imposed across a heat pipe, heat is conducted and convected across the heat pipe, allowing as much as 100× the heat transfer as may occur through conduction alone. An additional benefit of heat pipe technology is that, through control of the internal pressure at manufacturing, the heat pipe can be tuned to have a desired evaporation or condensation temperature. This makes it possible to provide a surface with a set constant temperature without any additional control or feedback. Thus, the heat pipe provides an additional advantage of reducing or eliminating any requirement to pump a coolant and provides a further advantage of having a heat exchanger surface with a constant wall temperature. This advantageously will allow production of even smaller and more portable slurry production systems and devices, as well as systems and devices that require fewer pumps and therefore require less electrical power to operate.

Figure 15:
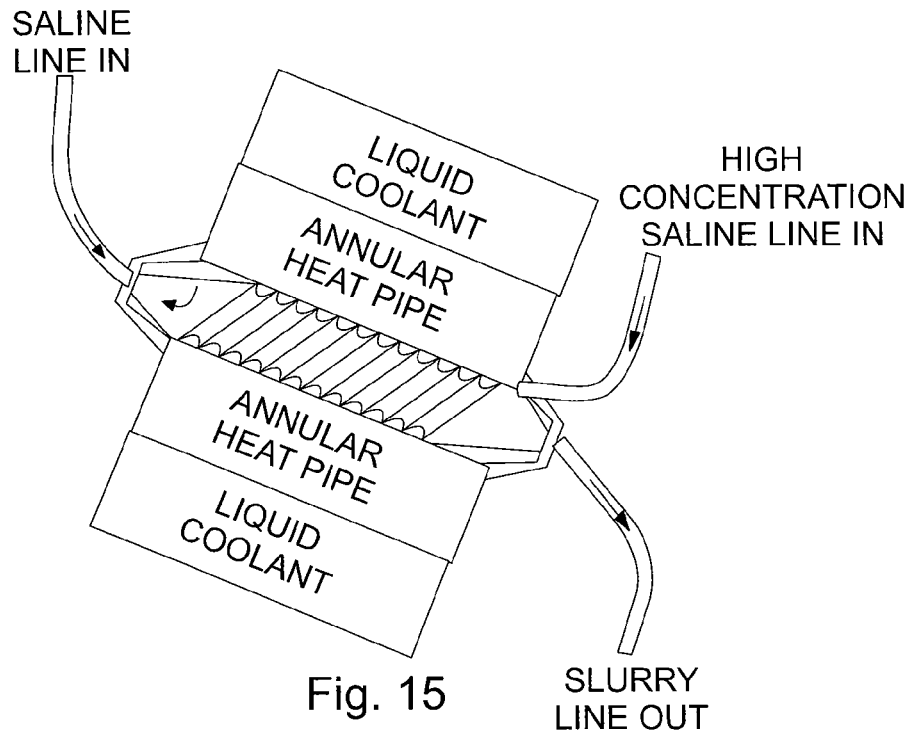
FIG. 15 shows an embodiment of a heat exchanger comprising an annular heat pipe that can be used in the coolant production assembly shown in FIG. 6.

An example of a heat pipe heat exchanger configuration is shown in FIG. 15, which provides a cross sectional view. The heat pipe is preferably annular, and in this view has been cut in half along the central axis. In the configuration shown, the liquid in the heat pipe condenses on the side of the coolant and then is wicked toward the saline side, where the coolant may evaporate. The evaporation temperature can be maintained between about 0° and about −20° C. The coolant can be a compressed gas such as liquid nitrogen, or it can be alcohol mixed with dry ice. The heat pipe can provide an even temperature at the saline side even if there are temperature gradients at the coolant side. The coolant can be contained in a second larger annulus in which the heat pipe nests.

Figure 16:
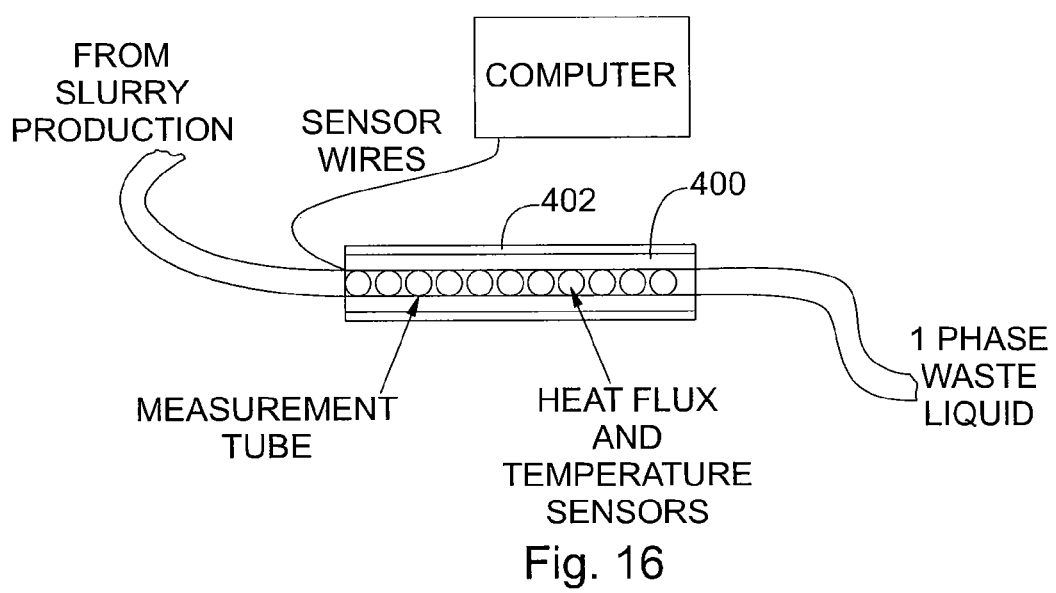
FIG. 16 shows a schematic diagram of an exemplary embodiment of a system to measure solid void fraction and particle size in a two-phase, liquid-solid coolant, which system comprises a heat pipe.

FIG. 16 illustrates a modification of the system shown in FIG. 2. In the cross sectional view of the system shown in FIG. 16, the heat pipe includes an annulus which has been cut in half along its central axis. In this configuration, the evaporative side of the heat pipe 400 can be proximal to the heater 402. The condensing side of the heat pipe can be proximal to the side of the slurry. The condensing liquid can heat the slurry melting the ice. The measurement techniques described above can be used. The condensation temperature can range from about 0° to about 60° C.

Systems and devices for producing ice slurry preferably will have monitoring instrumentation capable of identifying modes of failure upon processing and analysis to be completed either real time or after operation, and preferably will have appropriate mechanisms for responding to various modes of failure. The systems and devices can have performance standards set forth from calculations as well as experimental calibration, and deviations from these standards can be utilized to alter or control the operation of the device.

For example, uncharacteristic changes in heat flow can cause the system to systematically evaluate temperature, rotation rate, and torque, individually and/or then in combination, to identify the cause of the system failure. The cause can then optionally be translated and brought to the attention of the user so the failure can be addressed.

Temperature measuring devices can include, but are not limited to, thermocouples, non-limiting examples of which include K, J, T, and E type thermal resistive devices (RTD's), or infrared instrumentation. The rotary torque can be measured using a variety of methods, including moment arm, slip ring, and rotary transformer methods. The rotation rate sensor, or angular displacement sensor, can also utilize a variety of sensing methods and can operate in a variety of ranges. The instrumentation to measure rotation rate and rotary torque can be in the form of a single sensor, and can be provided with a variety of sensor ranges. Such instrumentation is known in the art. All measurements can be transmitted to a computer for data acquisition and analysis.

Ice slurry generating systems and devices preferably have a target heat transfer coefficient that can be altered by changing the mass flow rates in the system. Thus, optimal ice slurry production can have a target heat transfer coefficient that, if not met, will indicate a failure in the system.

Analysis of the coolant and ice slurry (product) temperatures, measured at either the inlet, outlet, or both, or at any other location, allows for system monitoring that can trigger operation of a failure mode should the coolant or product temperatures rise above or fall below a working or optimized range for the device. Such a failure mode will be comprised of adjustments in the operation of the system to bring the coolant and product temperatures within the appropriate range.

The rate of temperature change can also serve as an indicator of a failure mode. A change in the temperatures of the coolant and ice slurry product can result in a change of the heat transfer coefficient.

Other data points that can be subject to monitoring to optimize operation of the slurry production system include ice fouling from the exchanger. A change in the operation of ice removal can result in a change of the heat transfer coefficient. In addition, the generated slurry can be monitored based on at least three properties, individually or in any combination, including (1) ice mass concentration; (2) ice particle size; and (3) ice particle shape. These three properties can determine the rheologic properties of the slurry, the melt temperature range and the pump power requirements. Variations of these properties outside of accepted optimal ranges can trigger a series of adjustments designed to bring these properties of the ice slurry back to within acceptable ranges.

The invention also provides methods for producing an ice slurry using the ice slurry production systems described and exemplified herein. In some detailed aspects, the methods comprise contacting a fluid such as a low concentration saline solution with a heat exchanger for a time sufficient to allow a portion of the fluid to freeze and form an ice slurry, and then admixing a higher concentration saline solution with the ice slurry. The heat exchanger can comprise two concentric tubes, or it can be a heat pipe such as an annular heat pipe. The high concentration saline solution smoothes the formed ice crystals to allow the slurry to be pumpable. In an alternative aspect, the methods comprise contacting a fluid such as a lower concentration saline solution with a heat exchanger for a time sufficient to allow a portion of the fluid to freeze and form an ice slurry, and then contacting the ice slurry with a heat source for a period of time sufficient to smooth the ice crystals in the slurry. The methods can be used to produce ice slurry on any scale, small or large, for example, for administration to a patient, or for fire suppression or crowd control.

The invention also provides methods for using a two-phase coolant such as the ice slurry produced by the inventive ice slurry production systems and devices. The ice slurry can be used to cool or maintain a particular temperature in any application where lower temperatures or temperature maintenance is desired.

In a highly preferred aspect, the invention features methods for inducing or maintaining hypothermia in a subject comprising administering to a subject in need thereof a pharmaceutically acceptable ice slurry such as an ice slurry produced by the inventive ice slurry production systems and methods described or exemplified herein. The ice slurry is administered to the subject in an amount effective to induce or maintain hypothermia. The effective amount may be dependent on various factors. Non-limiting examples of such factors include the species, height, weight, age of the subject, condition being treated and the like. Administration can proceed by any means suitable for the particular application to which the coolant is being used. For example, the coolant can be administered intravenously, intramuscularly, topically, orally, nasopharyngeally, anally, vaginally, into intraperitoneal or intrathoracic spaces, into other physiological spaces or regions, and the like. Intravenous administration is highly preferred.

The methods can be used in any subject. Preferably, the methods are used in mammals such as horses, cows, pigs, dogs, cats, rabbits, rats, hamsters, and mice. The methods are preferably beneficially employed in humans.

The hypothermia can be systemic, meaning that hypothermia can be induced and/or maintained throughout the entire body of the subject. Alternatively, the hypothermia can be directed to a particular location or locations of the body, for example, to a particular organ, appendage, cavity, space, or region.

Also provided are methods for rapidly cooling or maintaining a cool temperature for perishable goods. Such methods generally comprise producing an ice slurry using any of the ice slurry production systems, devices, and methods described and exemplified herein, and exposing the perishable goods to the ice slurry. Non-limiting is examples of perishable goods include food products such as meats, fish, produce, milk and milk products, confectionaries, beverages, and the like; pharmaceuticals; vitamins; minerals; volatile chemicals; radionuclides; biomolecules such as nucleic acids, polypeptides, and lipids, cells, tissues, organs; and biological fluids such as blood, blood serum, urine, saliva, sweat, milk, and the like.

Also featured are methods for rapidly cooling heat generating devices such as a weapon. The methods comprise producing an ice slurry using any of the ice slurry production systems, devices, and methods described or exemplified herein, and exposing the weapon or components thereof to the ice slurry. Any weapon or sub-part of a weapon such as a gun barrel can be cooled using the inventive method. Non-limiting examples of suitable weapons include guns, cannons, and electromagnetic pulse generators. Weaponized lasers can also be cooled according to the inventive methods. The weapons can be hand-held, or they can be those attached to equipment such as a plane, helicopter, or vehicle.

The following examples are provided to describe exemplary aspects of the invention in greater detail. They are intended to illustrate, not to limit, the invention.

EXAMPLE 1

On-Demand Production of Saline Ice Slurry

In this prophetic example, a device is prepared for on-demand production of a micro-particulate two-phase (solid and fluid) coolant. The device includes two containers of fluid that may be separate or concentric. One container is pressurized and the other is not. The device is used to produce a uniform and homogenized saline ice slurry.

The container can be filled with water that can contain varying concentrations of salts, surfactants, and/or emulsifiers. The container will be pressurized to a level high enough to induce instantaneous expansion of the liquid upon release from the container. The pressurized container will not be entirely full of fluid, instead leaving a large volume, expected to be about 50%, to the gas phase. The pressurized container and its contents will then be refrigerated to a temperature below the atmospheric pressure freezing point of the fluid.

A specialized nozzle can be attached to the end of the pressurized container. This nozzle will create a fine mist of the fluid as the fluid is expelled from the bottle. As the pressure is released, the fluid will spontaneously change to the solid phase (e.g., freeze) because its temperature is held below its atmospheric pressure freezing point. The formed ice crystals will be processed in a homogenizer, where they will be mixed with a carrier fluid that was released from the second tank. Homogenization ensures tunable ice particle size and chemical smoothing.

The second container will contain a fluid compatible with the solidified fluid from the first container in order to form the desired ice slurry. For example, the second container can contain water, salts, surfactants and other emulsifiers. As above, the second container and its contents will be refrigerated to a temperature below the atmospheric pressure freezing point of the fluid from container 1. The fluid from the second container, however, will remain in the fluid phase, even at the low temperature, because of the absence of pressure.

The cooled fluid from the second container will then be pumped into the homogenizer and mixed with the ice particles created from the first container. The fluid thus will serve as a carrier fluid for the micro-particulate ice for delivery to a desired location and use for a desired purpose.

There can be a pressure connection between the homogenizer outlet and the second container. In this case, the excess pressure from the first container that was used to cause freezing point depression is used upon release to pump the fluid from the second container into the homogenizer. A schematic illustration is provided in FIG. 1.

EXAMPLE 2

Low-Electrical Production of On-Demand High or Low Volume Saline Ice Slurry

In this prophetic example, a device is prepared for on-demand production of a micro-particulate two-phase (solid and fluid) coolant in high or low volumes. The device may include large scale versions of the devices previously described as well as large volumes of primary coolant such as a compressed gas or dry ice. The primary separation between Example 1 and Example 2 is the provision or slurry without the requirement of electrical power.

In situations where the availability of electrical power may limit the previously described use of a two phase coolant the described devices and methods may be used to overcome the electrical power limitation. In this example, which is pictured in FIG. 5, one of the slurry production devices described herein has been scaled to sizes effective to the particular cooling tasks. In addition, an appropriate volume of primary coolant is also available. The primary coolant is pumped through the Coolant Heat exchanger where a secondary coolant is cooled to a similar or slightly warmer temperature. The secondary coolant is pumped or is wicked to the Slurry Production Device. In the slurry production device the secondary coolant cools the saline water to its freezing point. Ice is scraped off of the heat exchanger surface and ice nucleates in the bulk liquid. Ice particle size is controlled by ice scraper blades and mixing. The saline and slurry are pumped through the slurry production device and delivered by means appropriate to the task.

EXAMPLE 3

Quality of a Two-Phase (Solid-Liquid) Coolant

In this prophetic example, an in-line system is proposed for assuring the quality of a two-phase (solid-liquid) coolant delivery system, preferably just prior to the site of is coolant application. The system is intended to address the concern that the quality of the coolant will alter in transit from slurry creation to site of action due to melting of the solid phase.

The device will consist of a tube with known heat transfer characteristics that has a series of heat flux and temperature sensors embedded at predetermined positions along the length of the tube. The environment outside of the tube will be held at a known temperature. An aqueous ice slurry will be passed through the tube at a prescribed volumetric flow rate and the heat flux and temperature will be measured as a function of distance traveled by the coolant down the tube. The ice void fraction will be calculated by measuring the total amount of heat that will enter the coolant slurry. The ice particle size will be correlated from the time that was required to transfer that much heat. These calculations will be made on a computer connected to the series of sensors.

The calculation of the ice void fraction will be made as follows. The fluid will be well-mixed within the tube as a function of the tube design, and the temperature within the tube will stay very close to the freezing point of the liquid, until all of the ice is melted. The heat flux will therefore primarily go to the melting of the ice. Once the ice is melted the temperature of the liquid will begin to rise, and this will be detected by the temperature sensors. Therefore, based on the location of the initial rise in temperature of the fluid in the tube, the measured heat flux as a function of the length of the tube, and volumetric flow rate the ice percentage will be estimated using a relationship such as Equation 1:

$$\Delta Q_{slurry} = m_{slurry} C \Delta T + \%_{ice} m_{slurry} \lambda_{ice}$$

where $\Delta Q_{slurry}$ is the heat energy gained from the heater, $m_{slurry}$ is the mass of the slurry, C is the heat capacity of the liquid phase of the slurry, $\Delta T$ is the change of temperature of the slurry, $\%_{ice}$ is the ice percentage, and $\lambda_{ice}$ is the latent heat for the phase change from ice to liquid.

The calculation of the average ice particle size will come from an empirically-derived correlation. A heat transfer equation (Equation 2) that will explain the method for measuring the average slurry particle size is:

$$\dot{Q} = hA\Delta T$$

where $\dot{Q}$ is the heat entering the slurry in units of watts (heat flow), h is the convective heat transfer coefficient in units of $W/m^2K$, and $\Delta T$ is the temperature difference between the inner tube wall and the bulk fluid temperature. The coefficient h will be a function of the fluid volumetric flow rates and fluid physical properties as well as the size and distribution of the ice particles in the slurry. It is expected that the value of h will increase with decreasing average particle size when the ice percentage is fixed. As the particle size decreases, the number of particles will increase as will the interfacial area available for phase change from solid to liquid assuming that the volume is fixed. An example of the difference in the measured values that one may expect under these conditions is given in FIG. 3.

EXAMPLE 4

Heat Exchanger Construction and Ice Slurry Production

General Device Characteristics: A counter current scraped surface heat exchanger similar to the embodiment illustrated in FIG. 6 was constructed and used to generate ice slurry. The device had a heat exchange surface area of 0.011 $m^2$, an annular gap of 4.94 mm, and eight scraping blades.

The primary coolant was either 70% or 46% potassium formate. The primary coolant was cooled in a distinct heat exchanger loop composed of copper coils submerged in a dry ice/propanol mixture. The dry ice/propanol mixture created a uniform $-70°$ C. bath through which the potassium formate passed. The potassium formate entered the counter current heat exchanging device at a temperature below the freezing point of the product. The product in the cases presented is either 10% NaCl by mass (10% saline) or 1% NaCl by mass (1% saline).

All exposed lines were insulated. The range of mass flow rates for coolant and product were (respectively): 0.011-0.002 [kg/sec] and 0.006-0.001 [kg/sec]. In general, the product entered the counter current heat exchanger at room temperature. The central impeller shaft was rotated at a constant 100 rpm.

The heat flow of the system, when no ice was being produced, was calculated using the following equation (Equation 3):

$$\text{HeatFlux} = \dot{Q} = C_p \dot{m}(T_{out} - T_{in})$$

where $C_p$ is the specific heat and $\dot{m}$ is the mass flow rate in [kg/sec]. The temperatures of the coolant ($T_{in}$ and $T_{out}$) and the product ($T_{in}$ and $T_{out}$) were measured with K type thermocouples and were recorded with a Sper Scientific 4 Channel Datalogging Thermometer. If the event included the generation of ice, the following equation (Equation 4) was used to obtain a representational heat flux:

$$\text{HeatFlux}_{consideringIce} = \dot{Q} = (C_p \dot{m}(T_{out} - T_{in}))(100 - \%_{ice}) + \dot{m}\lambda\%_{ice}$$

where $\lambda$ is the latent heat for the phase change from ice to liquid.

Ice Slurry Production. The scraped surface heat exchanger described above was used to produce ice slurry. The coolant was 70% potassium formate and the product was 10% NaCl.

Figure 17A:
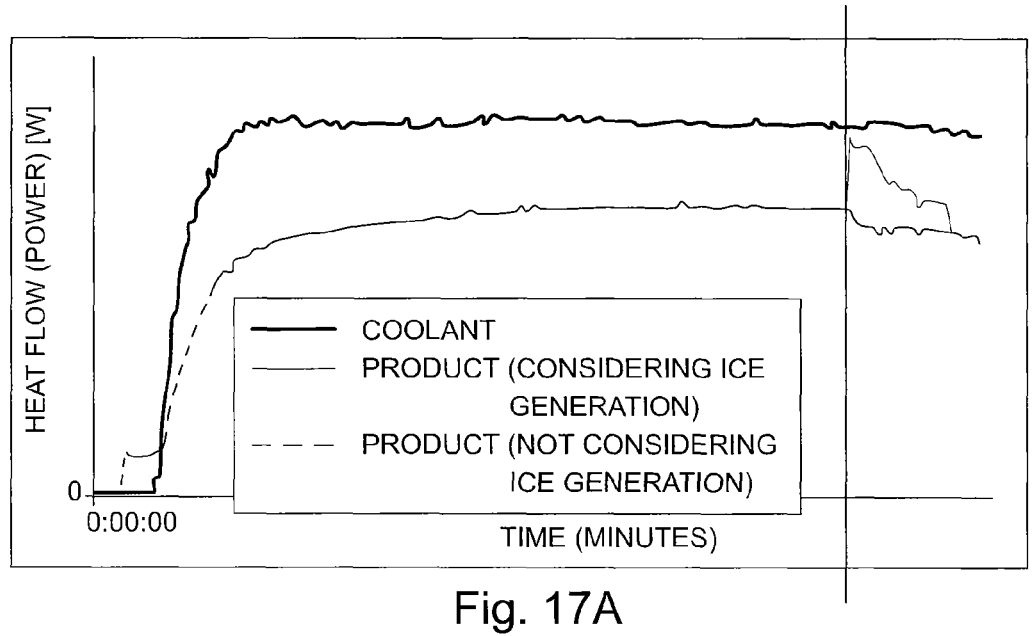
FIG. 17A-B shows the heat flow and temperature profile generated by the creation of slurry from a heat exchange device.
Figure 17B:
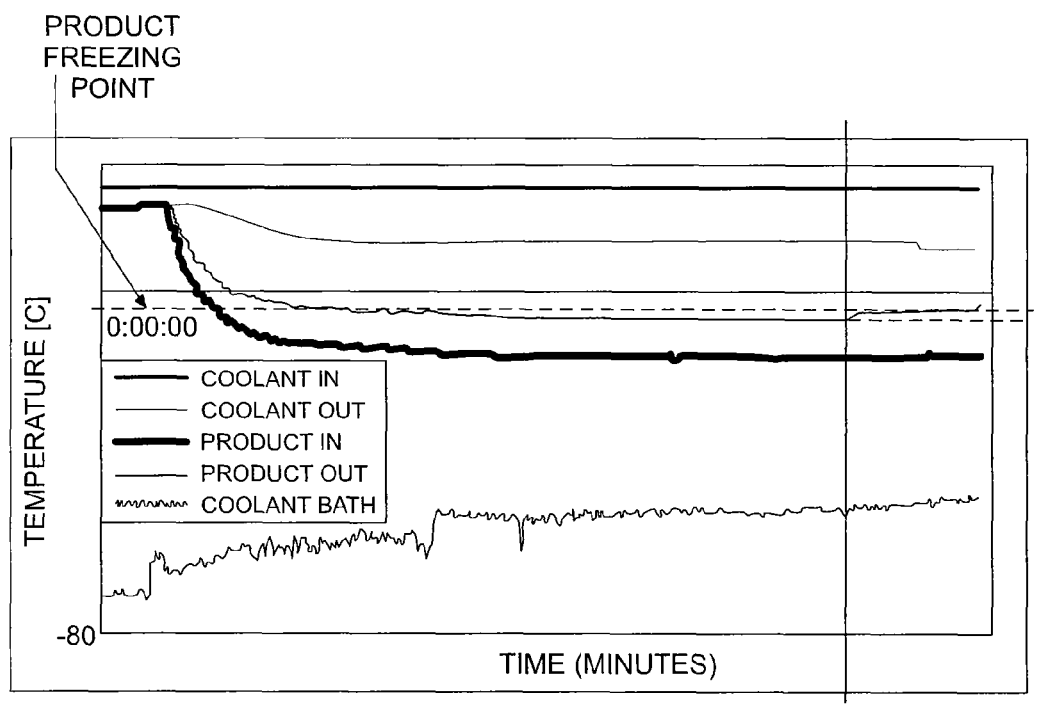

FIG. 17A shows the heat flow data for both the coolant and product, as derived using Equations 3 and 4. FIG. 17B traces the temperature profiles as a function of time. The temperature plot (FIG. 17B) shows the product was supercooled below the is freezing point; the degree of supercooling, in part, determines the concentration of ice produced during spontaneous generation. Spontaneous generation of ice particles occurred (indicated temporally by the vertical line in FIG. 17A-B) and the temperature of the product out increases, indicating the release of the heat of fusion to make the ice. FIG. 17A shows this by indicating an increase in the heat flow of the product out by the concentration of ice produced. The product out temperature remained at the freezing point of the product, and scraping of ice particles from the heat exchanger wall occurred after the spontaneous generation event.

Failure Mode Identification: The device had monitoring instrumentation capable of identifying modes of failure upon processing and analysis. The physical device had performance standards set forth from calculations as well as experimental calibration, and deviations from these standards were utilized to alarm the user to a change in the operation of the device. Uncharacteristic changes in heat flow prompted a systematic evaluation of temperature, rotation rate, and torque (individually and then in concert) to identify the cause of the system failure.

FIG. 18 shows a representative data set from the scraped surface heat exchanger for which a failure occurred in the form of a frozen coolant line. The coolant was 46% potassium formate and the product was 1% NaCl.

Figure 18A:
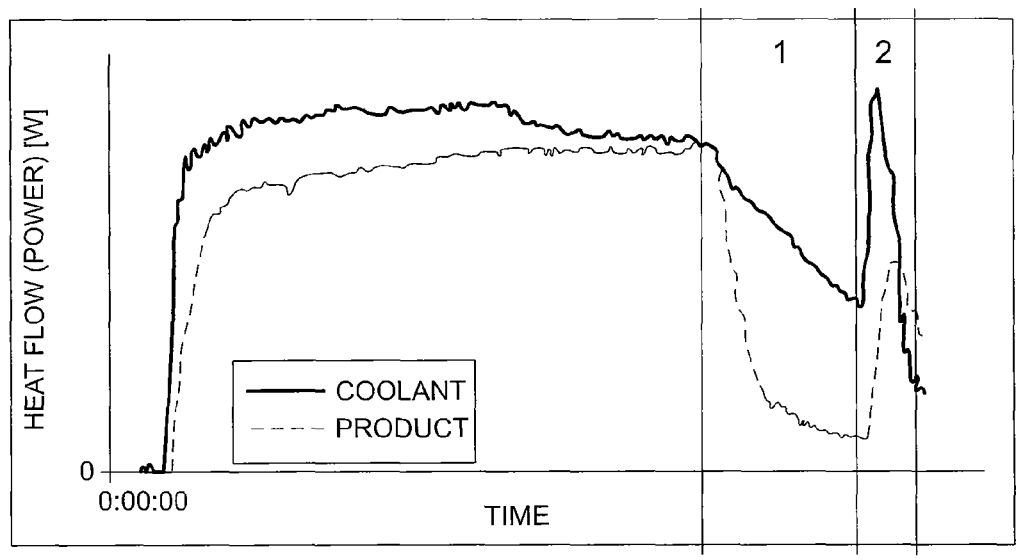
FIG. 18A-B shows the heat flow and temperature profiles illustrating the effect of a frozen plug in the coolant lines on the operation of a slurry production system.
Figure 18B:
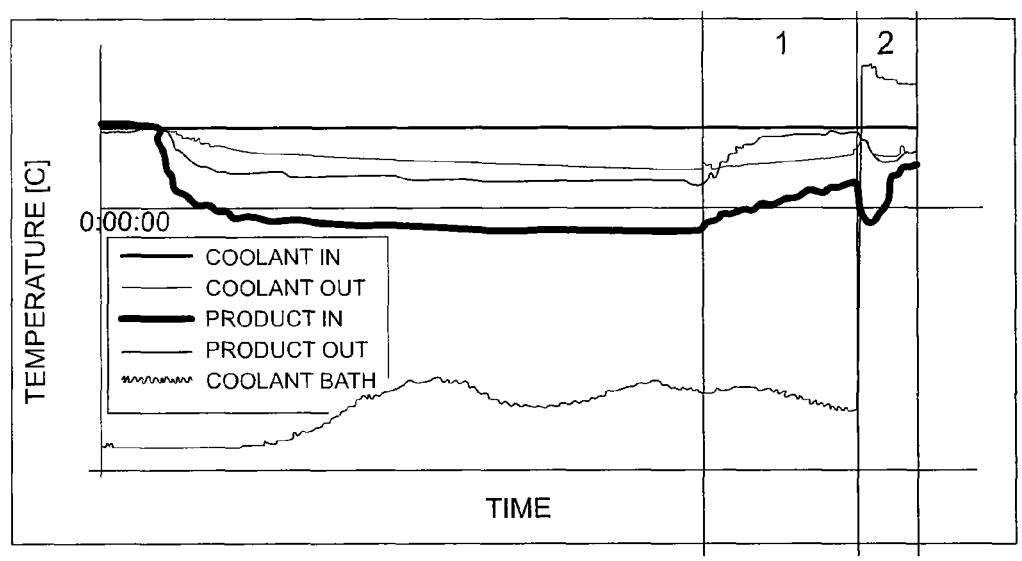

Section 1 of FIG. 18A shows a large change in the heat flow of the system for both the coolant and the product. This change was accompanied by a dramatic rise in the product out temperature as well as the coolant in temperature, while the coolant bath temperature remained constant (indicating the bath was not exchanging heat with the coolant) (FIG. 18B). The increase in coolant bath temperature, shown in section 2, was then correlated with a decrease in coolant in temperature, indicating the release of a frozen plug from the coolant lines.

Figure 19A:
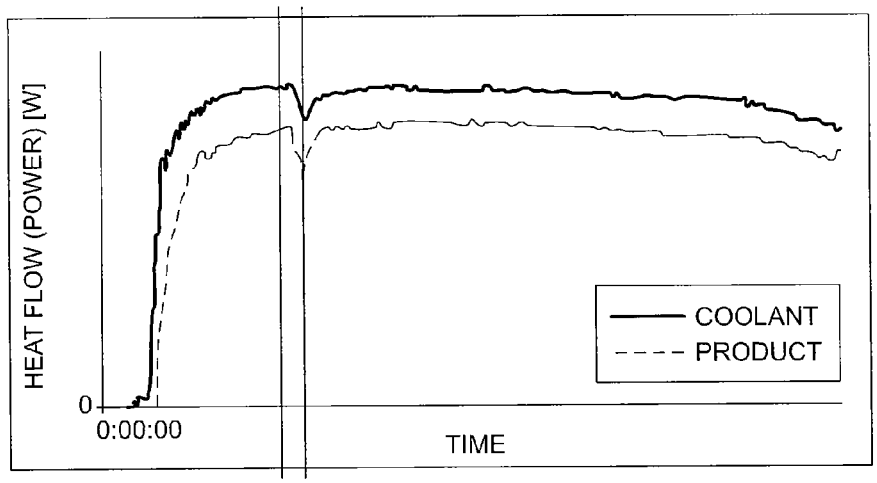
FIG. 19A-C shows the heat flow and temperature profile illustrating the effect of a change in rotation rate of ice scraper blades on the operation of an ice slurry production system.
Figure 19B:
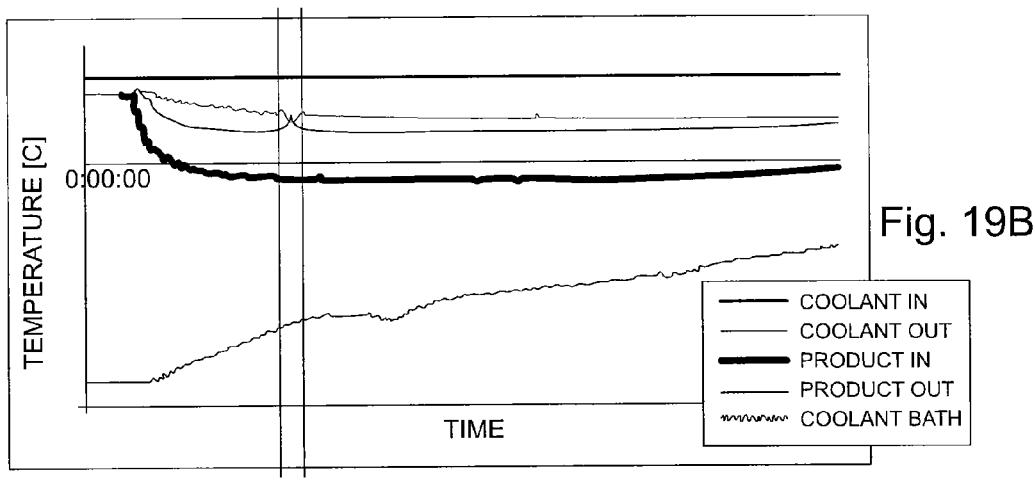
Figure 19C:
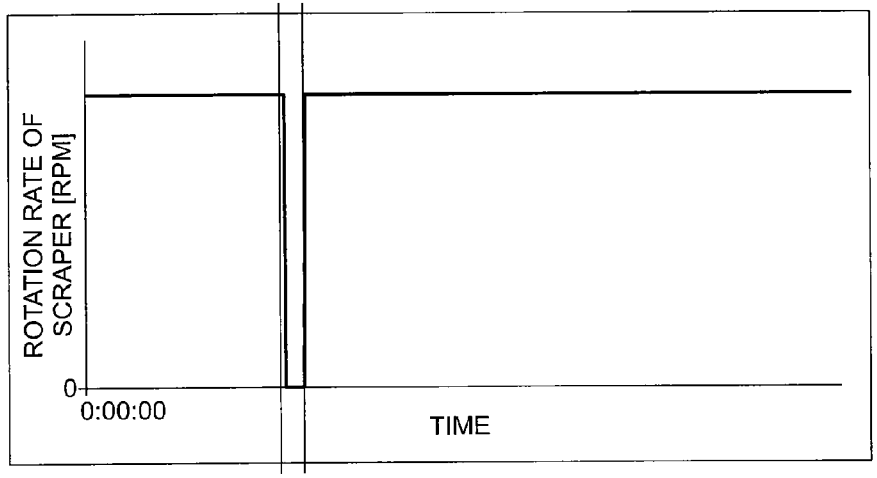

FIG. 19A-C shows a representative data set illustrating failure in the form of a defective methodology for removing ice from the heat exchanging surface. The coolant was 46% potassium formate and the product was 1% NaCl.

FIG. 19A shows a change in the heat flow of the system similar to FIG. 18A-B; however, it was not correlated with a large change in the entering coolant temperature, and the coolant bath temperature continued to change (indicating heat was being exchanged with the coolant). The change in heat flow was accompanied by a rise in the product out temperature (FIG. 19B) as well as a decrease in the coolant out temperature. FIG. 19C is a representation of what occurred to the scraper rotation rate during the drop in heat flow shown in FIG. 19A; the correlation in time indicates that the change in heat flow was a result of the change in scraper rotation rate.

The present invention is not limited to the embodiments described and exemplified above, but is capable of variation and modification within the scope and range of equivalents of the appended claims.

What is claimed is:

1. A device for producing an ice slurry, comprising:
    a housing comprising a heat exchanger, wherein the heat exchanger comprises at least one coolant and is configured to control the freezing temperature of a fluid;
    a driveshaft;
    at least one scraper blade coupled to the driveshaft, wherein the blade is configured to scrape ice from the side walls of the heat exchanger;
    an internal disk coupled to the distal end of the heat exchanger, wherein the internal disk is configured to hold a bearing positioned at a distal end of the driveshaft;
    a mixing vessel housing coupled to the housing comprising the heat exchanger, wherein the mixing vessel housing comprises a mixing vessel configured to receive ice slurry from the heat exchanger and to receive a high concentration saline solution, wherein the mixing vessel comprises a mixing blade.

2. The device of claim 1, wherein the heat exchanger comprises two concentric tubes, wherein the inner tube comprises a lumen through which the fluid flows, and wherein the outer tube comprises a lumen accommodating the inner tube and the coolant.

3. The device of claim 1, wherein the fluid is a physiological saline solution.

4. The device of claim 1, wherein the coolant is dry ice or a compressed gas.

5. The device of claim 1, wherein the heat exchanger comprises a heat pipe.

6. The device of claim 1, wherein the ice slurry comprises about 30% to about 70% ice.

7. The device of claim 1, further comprising a first pump, wherein the first pump is configured to transport the ice slurry through one or more components of the device.

8. The device of claim 1, further comprising a second pump, wherein the second pump is configured to pump the coolant through the heat exchanger.

9. A method for producing an ice slurry, comprising the steps of:
    contacting a low concentration saline solution with a heat exchanger, wherein the heat exchanger comprises at least one coolant and is configured to control the freezing temperature of the saline solution, and wherein a portion of the saline solution freezes within the heat exchanger and the remainder of the saline solution remains in the liquid state to form the ice slurry; and
    admixing a high concentration saline solution with the ice slurry.

10. The method of claim 9, wherein the heat exchanger comprises two concentric tubes, wherein the inner tube comprises a lumen through which the low concentration saline solution flows, and wherein the outer tube comprises a lumen accommodating the inner tube and the coolant.

11. The method of claim 9, wherein the heat exchanger comprises a heat pipe.

12. The method of claim 9, wherein the low concentration saline solution is a physiological saline solution.

13. The method of claim 9, wherein the ice slurry comprises about 30% to about 70% ice.

* * * * *